US009011354B2

(12) United States Patent
Angold et al.

(10) Patent No.: US 9,011,354 B2

(45) Date of Patent: Apr. 21, 2015

(54) HIP AND KNEE ACTUATION SYSTEMS FOR LOWER LIMB ORTHOTIC DEVICES

(75) Inventors: Russdon Angold, American Canyon, CA (US); Adam Brian Zoss, Berkeley, CA (US); Jon William Burns, Richmond, CA (US); Nathan Herbert Harding, Oakland, CA (US)

(73) Assignee: Ekso Bionics, Inc., Richmond, CA (US)

( * ) Notice: Subject to any disclaimer, the term of this patent is extended or adjusted under 35 U.S.C. 154(b) by 1005 days.

(21) Appl. No.: 13/119,075

(22) PCT Filed: Sep. 24, 2009

(86) PCT No.: PCT/US2009/058199

§ 371 (c)(1),
(2), (4) Date: Mar. 15, 2011

(87) PCT Pub. No.: WO2010/036791

PCT Pub. Date: Apr. 1, 2010

(65) Prior Publication Data

US 2011/0166489 A1 Jul. 7, 2011

Related U.S. Application Data

(60) Provisional application No. 61/099,817, filed on Sep. 24, 2008.

(51) Int. Cl.

| | |
|---|---|
| ***A61H 3/00*** | (2006.01) |
| ***A61F 5/00*** | (2006.01) |
| ***A61H 1/02*** | (2006.01) |

(52) U.S. Cl.

CPC .............. *A61H 3/008* (2013.01); *A61H 1/0255* (2013.01); *A61H 2201/1246* (2013.01);

(Continued)

(58) Field of Classification Search

CPC ......... A61H 1/00; A61H 1/0262; A61H 3/00; A61H 5/00; A61H 5/01; A61H 2005/0132; A61H 2005/0144; A61H 2/644; A61H 2/646; A61H 2/605

USPC ....................... 601/33–35; 602/16, 23, 24, 26

See application file for complete search history.

(56) References Cited

U.S. PATENT DOCUMENTS

| | | | | |
|---|---|---|---|---|
| 3,976,057 | A * | 8/1976 | Barclay | 601/34 |
| 4,064,569 | A * | 12/1977 | Campbell | 623/43 |

(Continued)

FOREIGN PATENT DOCUMENTS

| | | |
|---|---|---|
| EP | 1260201 | 11/2002 |
| WO | WO 2007/088044 | 8/2007 |

(Continued)

*Primary Examiner* — Justine Yu

*Assistant Examiner* — Christopher Miller

(74) *Attorney, Agent, or Firm* — Diederiks & Whitelaw, PLC

(57) ABSTRACT

A lower limb orthotic device includes a thigh link connected to a hip link through a hip joint, a hip torque generator including a hip actuator and a first mechanical transmission mechanism interposed between the thigh link and the hip link, a shank link connected to the thigh link through a knee joint, a knee torque generator including a knee actuator and a second mechanical transmission mechanism interposed between the thigh link and the shank link, and a controller, such as for a common motor and pump connected to the hip and knee torque generators, for regulating relative positions of the various components in order to power a user through a natural walking motion, with the first and second mechanical transmission mechanisms aiding in evening out torque over the ranges of motion, while also increasing the range of motion where the torque generators can produce a non-zero torque.

29 Claims, 19 Drawing Sheets

(52) U.S. Cl.
CPC ............ *A61H 2201/14* (2013.01); *A61H 1/024* (2013.01); *A61H 1/0244* (2013.01); *A61H 3/00* (2013.01); *A61H 2201/123* (2013.01); *A61H 2201/1238* (2013.01); *A61H 2201/1642* (2013.01); *A61H 2201/165* (2013.01); *A61H 2201/1676* (2013.01)

(56) References Cited

U.S. PATENT DOCUMENTS

| | | | | |
|---|---|---|---|---|
| 4,215,442 | A * | 8/1980 | Blatchford et al. | 623/39 |
| 4,523,585 | A * | 6/1985 | Lamb et al. | 602/16 |
| 4,557,257 | A | 12/1985 | Fernandez et al. | |
| 5,282,460 | A | 2/1994 | Boldt | |
| 5,337,737 | A * | 8/1994 | Rubin et al. | 601/33 |
| 5,411,482 | A * | 5/1995 | Campbell | 604/153 |
| 5,664,477 | A * | 9/1997 | Koehler | 91/529 |
| 6,187,052 | B1 * | 2/2001 | Molino et al. | 623/52 |
| 6,914,406 | B1 | 7/2005 | Wilkes et al. | |
| 7,153,242 | B2 | 12/2006 | Goffer | |
| 7,153,243 | B1 | 12/2006 | Krull | |
| 7,190,141 | B1 | 3/2007 | Ashrafiuon et al. | |
| 7,481,742 | B2 * | 1/2009 | Katoh et al. | 482/51 |
| 7,524,297 | B2 | 4/2009 | Shimada et al. | |
| 7,628,766 | B1 | 12/2009 | Kazerooni et al. | |
| 7,785,279 | B2 | 8/2010 | Sankai | |
| 2007/0056592 | A1 * | 3/2007 | Angold et al. | 128/845 |
| 2007/0123997 | A1 | 5/2007 | Herr et al. | |
| 2007/0208430 | A1 * | 9/2007 | Gramnas | 623/39 |
| 2008/0022672 | A1 * | 1/2008 | He | 60/413 |
| 2008/0086088 | A1 * | 4/2008 | Malcolm | 604/151 |
| 2010/0094185 | A1 | 4/2010 | Amundson et al. | |

FOREIGN PATENT DOCUMENTS

| | | |
|---|---|---|
| WO | WO 2010/011848 | 1/2010 |
| WO | WO 2010/019300 | 2/2010 |

* cited by examiner

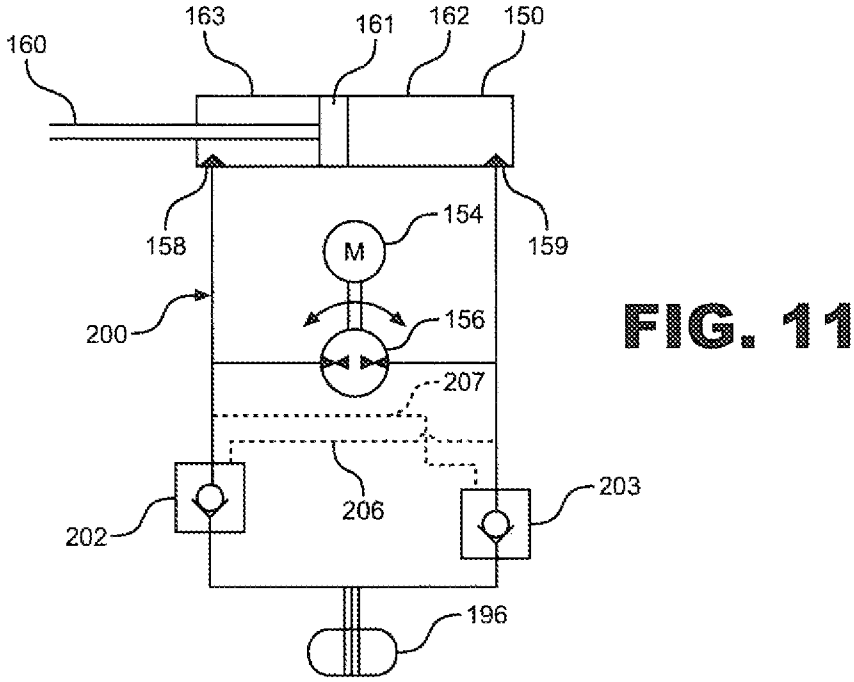
FIG. 11
FIG. 12
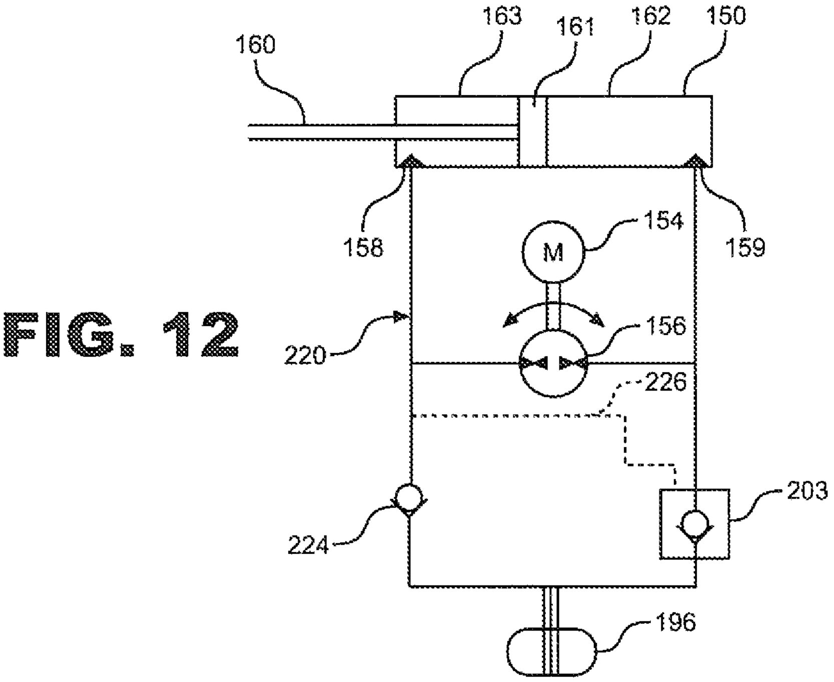

HIP AND KNEE ACTUATION SYSTEMS FOR LOWER LIMB ORTHOTIC DEVICES

CROSS-REFERENCE TO RELATED APPLICATIONS

This application represents a National Stage application of PCT/US2009/058199 entitled "Hip and Knee Actuation Systems for Lower Limb Orthotic Devices" filed Sep. 24, 2009, pending which claims the benefit of U.S. Provisional Patent Application Ser. No. 61/099,817 entitled "Hip and Knee Actuation for Orthotic Devices", filed Sep. 24, 2008.

BACKGROUND OF THE INVENTION

The present invention relates to the field of powered orthotics.

In general, devices for aiding crippled persons in walking are known in the art, as demonstrated by U.S. Pat. No. 4,557, 257 to Fernandez. However, such devices are bulky and burdensome to manipulate. Other systems, such as the Lower Extremity Exoskeleton set forth in U.S. Patent Application Publication No. 2006/0260620, establish a means for providing power at a knee joint. However, there is still seen to exist a need for an orthotic device which can be made compact and wearable by a person, but also provides the power necessary to aid a person in carrying a load. Additionally, there is seen to exist, a need for an orthotic device which powers both a thigh joint and a knee joint in a manner which aids a person in performing a natural walking motion.

SUMMARY OF THE INVENTION

In general, the present invention is directed to lower limb orthotic devices and, more specifically, to hip and knee actuation systems for orthotic devices. In particular, a lower, limb orthotic device to be worn by a user includes a thigh link adapted to couple to a user's lower limb; a hip link; a hip joint rotatably coupling the thigh link and the hip link to allow flexion and extension between the thigh link and the hip link; a power source; and a hip torque generator coupled to the thigh link and the hip link. In a preferred form, the hip torque generator includes a linear hydraulic hip actuator including a piston; a mechanical transmission mechanism connecting the linear hydraulic hip actuator to the thigh link; an eidetic motor; and a hydraulic pump driven by the electric motor to, pressurize hydraulic fluid within a hydraulic circuit to extend or retract the linear hydraulic hip actuator. Preferably, the orthotic device also includes a knee torque generator coupled to the thigh link and a shank link. The knee torque generator preferably includes a linear hydraulic knee actuator including a piston; a mechanical transmission mechanism connecting the linear hydraulic knee actuator to the shank link; and a hydraulic valve located between the linear hydraulic knee actuator and the hydraulic circuit to regulate the flow of hydraulic fluid between the linear hydraulic knee actuator and the hydraulic circuit. The hydraulic valve can be in the form of a three or four-port valve.

The hydraulic circuit can take on a variety of forms. In one preferred embodiment, the hydraulic circuit includes first and second pilot check valves which regulate the flow of hydraulic fluid between first and second fluid ports of a non-symmetrical linear hip actuator, a non-symmetrical linear knee actuator and a fluid, reservoir, while a three-port valve regulates fluid flow between the non-symmetrical linear knee actuator and the hydraulic circuit with this configuration, the hydraulic circuit provides different effective gear ratios such that the hydraulic pump turns at a first rate order to extend the piston of the hydraulic hip actuator and at a second rate in order to retract the piston at the same speed, and wherein the gear ratio allows for fast motion at low torque during a swing phase of the orthotic device and a slower motion at high torque during a stance phase of the orthotic device. In any case, the overall lower limb orthotic device employs a common motor driven pump arrangement for both hip and knee torque generators to power a user through a natural walking, motion, with the first and second mechanical transmission mechanisms aiding in evening out torque over the ranges of motion for the joints of the device, while also increasing the range of motion where the torque generators can produce a non-zero torque. Additional objects, features and advantages will become more readily apparent from the following detailed description made with reference to the drawings wherein like reference numerals refer to corresponding parts in the several views.

BRIEF DESCRIPTION OF THE DRAWINGS

FIG. 11 is a diagram of a hydraulic circuit including first and second cheek valves connected to the non-symmetrical linear hydraulic hip actuator;

FIG. 12 is a diagram of a hydraulic circuit including a pilot check valve connected to the non-symmetrical linear hydraulic hip actuator;

DETAILED DESCRIPTION OF THE PREFERRED EMBODIMENTS

Figure 1:
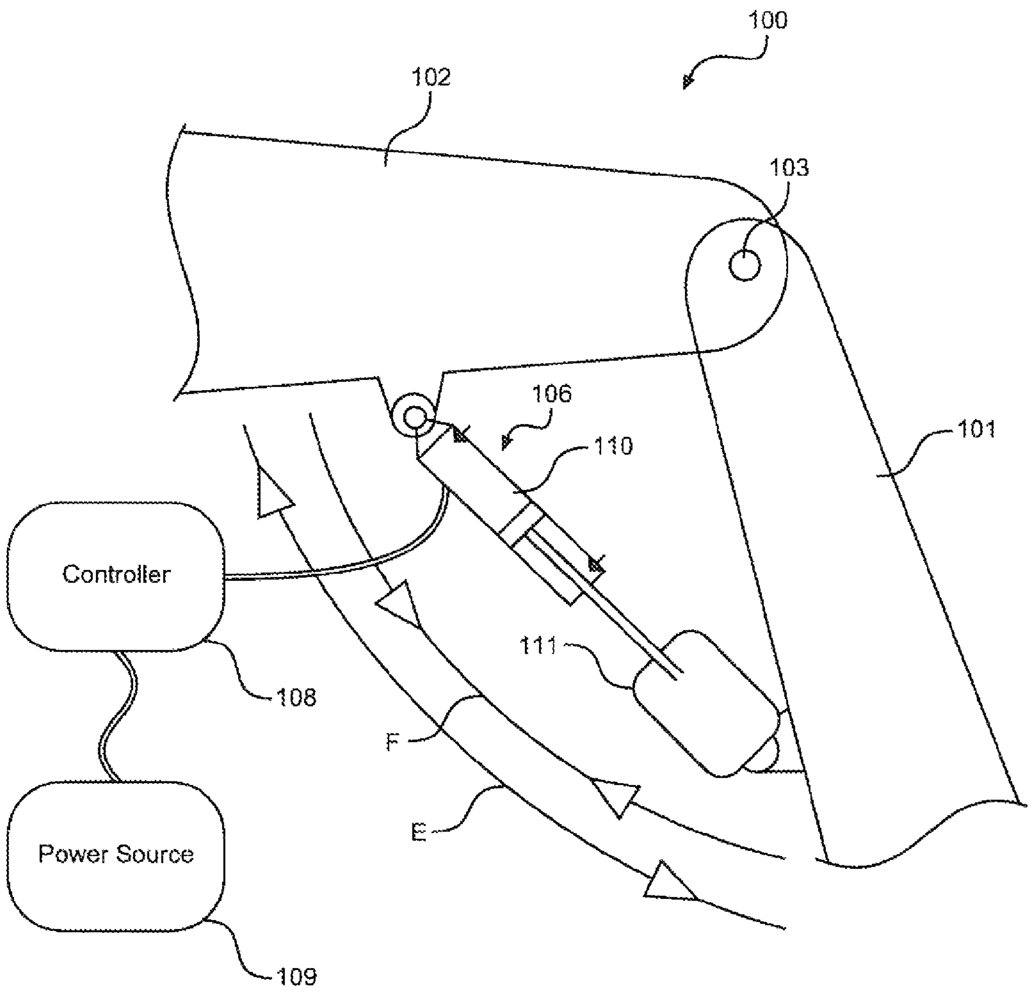
FIG. 1 is a partial side view of a lower limb orthotic device of the present invention including a hip torque generator.
Figure 2:
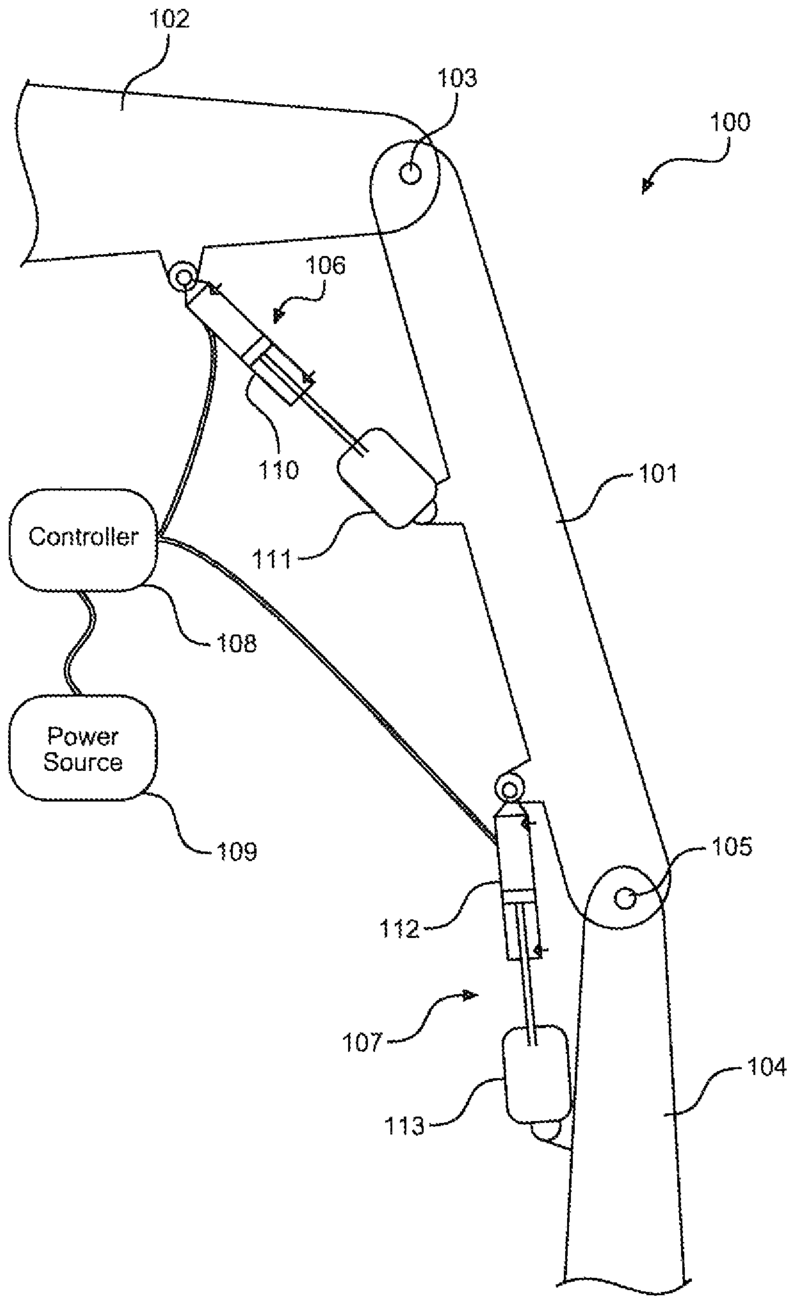
FIG. 2 is a partial side view of the lower limb orthotic device of FIG. 1, including a knee torque generator.

With initial reference to FIGS. 1 and 2, shown is a hip powered leg orthotic device 100, which is configured to be worn by a person and coupled to the person's lower limb. The orthotic contains at least a thigh link 101, and a hip link 102 that roughly correspond with a wearer's thigh and hips respectively. Although not depicted, it should be understood that straps or other devices may be utilized to connect orthotic device 100 to the wearer. Thigh link 101 and hip link 102 are connected by a hip jam 103. At minimum, hip joint 103 allows for extension and flexion along the sagittal plane of a person's body, but may allow additional degrees of freedom. The sagittal plane of a person's body should be understood to mean the imaginary plane that travels vertically from the top to the bottom of the body along the Y axis, dividing it into left and right portions. With reference, to FIG. 1, the hip extension direction is, depicted by arrow E and the hip flexion direction is depicted by arrow F. As depicted in FIG. 2, leg orthotic device 100 may also have a shank link 104 that corresponds with a person's shank. Shank link 104 is connected to thigh link 101 by a knee joint 105.

In general, the overall goal of the powered leg orthotic device 100 is to produce torque about the orthotic's, joints 103, 105 to move the orthotic's links 101, 102, 104 as desired. This is accomplished using first and second torque generators 106 and 107 to selectively create torque about respective joints, 103 and 105 of orthotic device 100. More specifically, first torque generator 106 produces torque, about hip joint 103 along the sagittal plane, while second torque generator 107 produces torque about knee joint 105 along the sagittal plane. The appropriate control signals are sent to torque generators 106 and 107 from a controller 108. A power source 109 supplies electric power necessary to drive controller 108 and respective torque generators 106 and 107. Examples of possible power sources include, without limitation, batteries, fuel cells, a sterling engine coupled to a generator, an internal combustion engine coupled to a generator, solar panels, or any combination thereof. In a preferred embodiment, the hip torque generator, 106 is in the form of a linear actuator 110 coupled to a hip mechanical transmission mechanism 111, and the knee torque generator 107 is likewise in the form of a linear actuator 112 coupled to a knee mechanical transmission mechanism 113.

Hip Actuator

First torque generator 106 may be implemented with either a rotary actuator (not shown) or linear actuator 110 and is coupled with hip mechanical transmission mechanism 111. Linear actuator 110 is preferred because it can be more compactly packaged and is more easily achieved with hydraulics (both of these advantages are discussed further below). Examples of linear actuators include, without limitation, linear hydraulic cylinders, electric motors coupled with ball screw mechanisms, linear, electric motors, pneumatic muscle actuators, and electro-active polymers.

Figure 3:
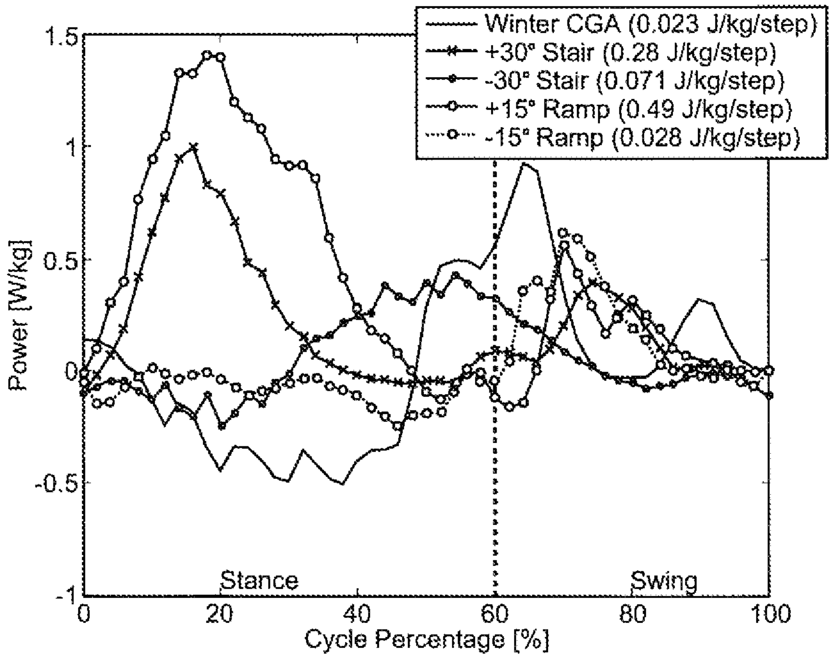
FIG. 3 illustrates the mechanical power used by a typical person while walking on level ground, on stairs and on a ramp.

FIG. 3 illustrates the mechanical power used by a typical person while walking on level ground, up and down a 30 degree staircase, and up and down a 15 degree ramp. This data is from clinical gait analysis recorded from biomechanics laboratories at well-known universities. Compared with the knee, joint and ankle joint the human hip joint is unique because it requires a substantial amount of positive power during both swing and stance. To match the strength of a person's hip muscles, linear actuator 110 is preferably able to put out a least 1.5 W/kg (kg of body weight) of power peak and 0.5 W/kg of power continuously.

Mechanical Transmission Mechanism

Figure 4:
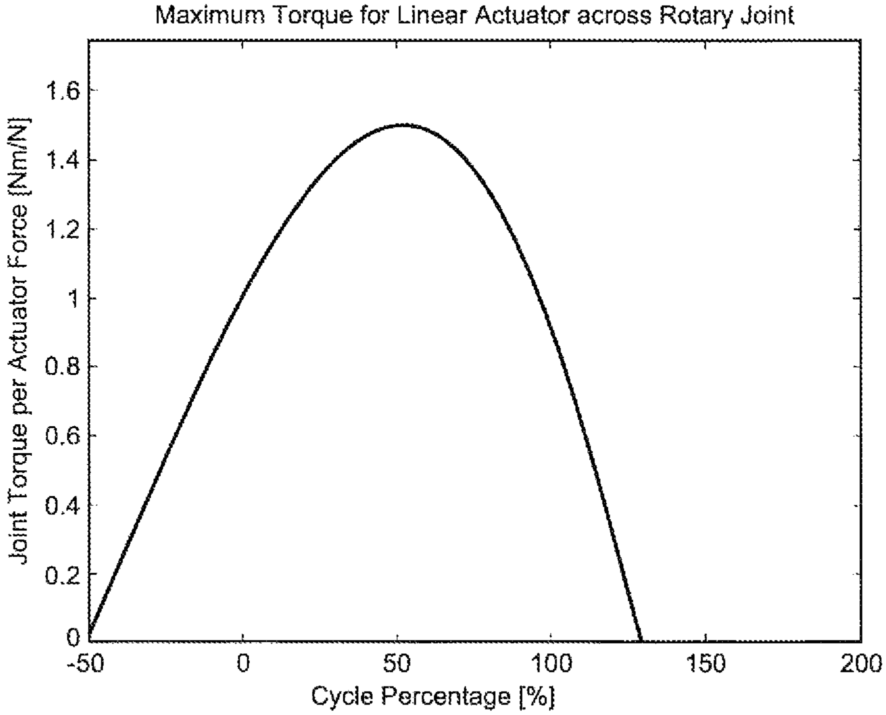
FIG. 4 illustrates torque generated by a linear actuator directly connected to a hip link and a thigh link without a mechanical transmission mechanism.

The main benefits of using hip and knee mechanical transmission mechanisms 111, 113 with linear actuators 110, 112 are to provide a more constant torque over the range of motion of an associated joint and to increase the range of motion where the joint's torque generator 106, 107 can produce a non-zero torque. Examples of mechanical transmission mechanisms that, can be used with linear actuators include, without limitation, a mechanical linkage, gear system, belt and pulley, and tendons. If linear hip, actuator 110 is directly connected to hip link 102 and thigh link 101 (without a mechanical transmission mechanism) then the maximum torque it can generate varies greatly as a function of joint angle as illustrated in FIG. 4.

Figure 5:
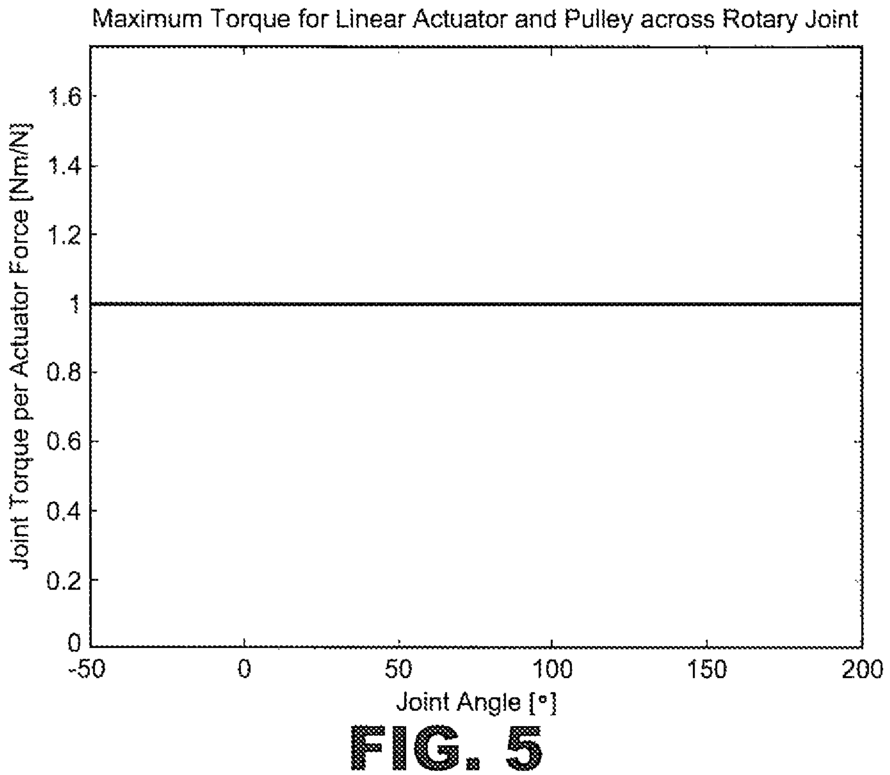
FIG. 5 illustrates torque generated by a linear actuator connected to a hip link and a thigh link with a pulley.
Figure 6:
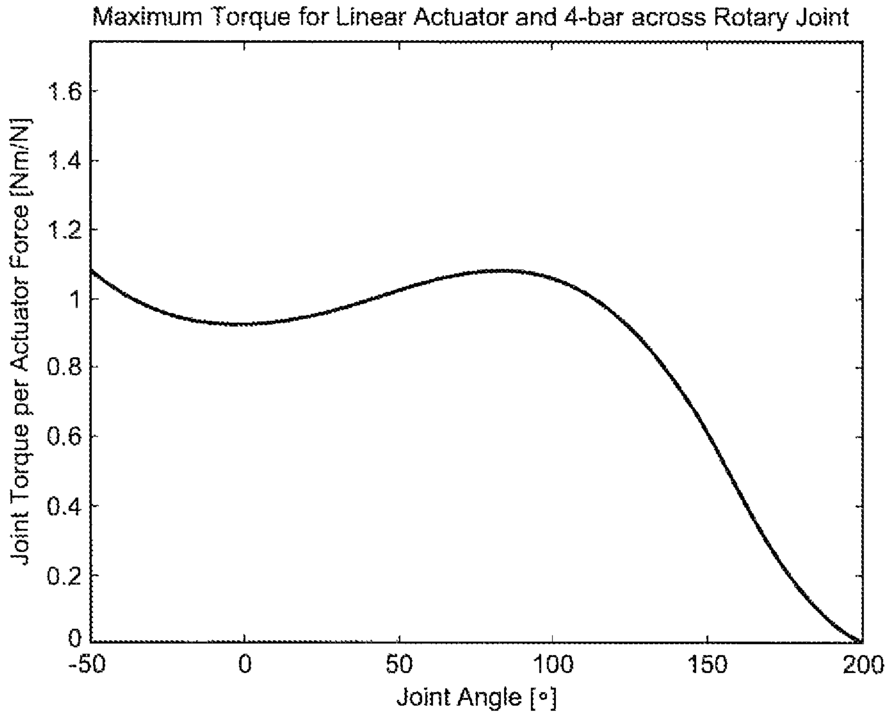
FIG. 6 illustrates torque generated by a linear actuator connected to a hip link and a thigh link with a four-bar mechanism of the present invention.

FIGS. 5 and 6 illustrate how the torque of linear actuator 110 can vary less when linear actuator 110 is connected to various mechanical transmission mechanisms, such as transmission mechanism 111. In particular, it should be noted how the range of motion where the joint torque remains non-zero also increases with appropriate mechanical transmission mechanism design.

Figure 7:
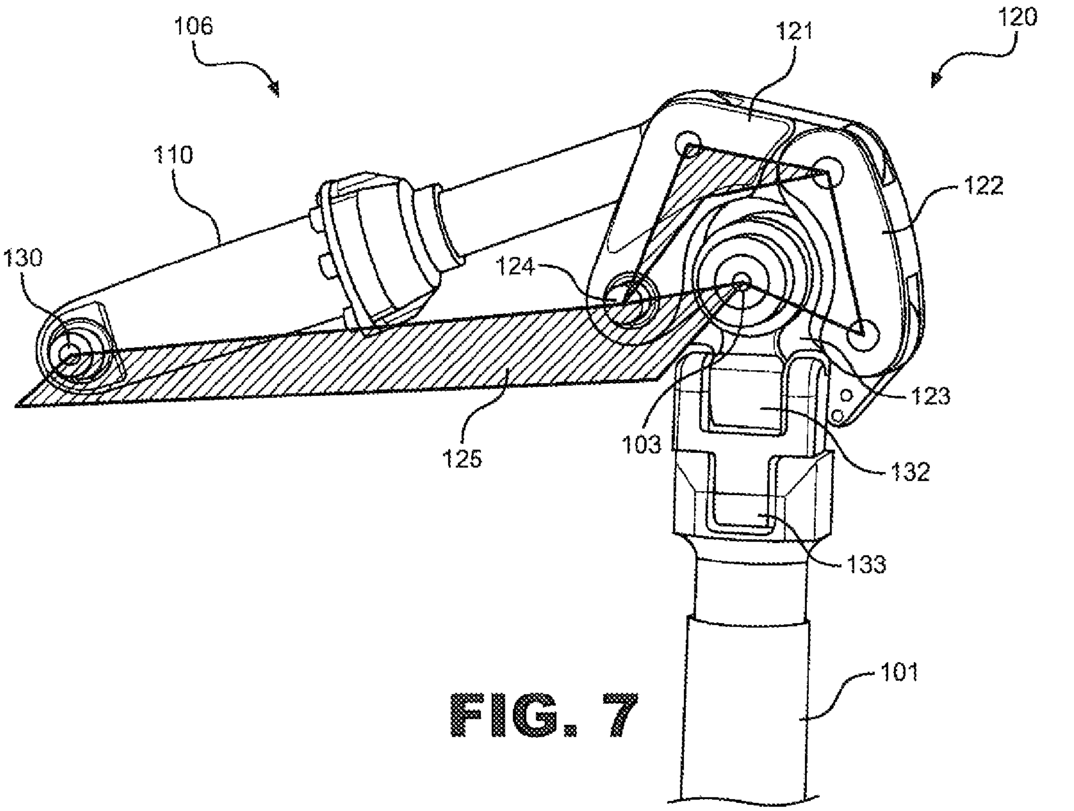
FIG. 7 is a side view of a hydraulic hip actuator of die present invention connected to a thigh link via the four-bar mechanism of the present invention.

As shown in FIG. 7, a preferred embodiment of mechanical transmission mechanism 111 is in the form of a four-bar linkage 120. Four-bar linkage 120 is made up of three moving links 121, 122 and 121. A fixed pivot 124 is established with respect to hip joint 103 by a fourth link 125. The fourth link 125 would typically be in the form of a housing for mechanical transmission mechanism 111 and would also mount a rear pivot point 130 for hip torque generator 106. For clarity, only pivots 103, 124 and 130 are fixed to this housing or fourth link 125. Other pivots that can be seen between link 123 and thigh link 101 are hip abduction and adduction joints 132, 133 as detailed in U.S. Patent Application Publication No. 2007/0056592 which is incorporated herein by reference. The four-bar linkage 120 allows the torque of actuator 110 to vary less as a function, of joint angle and can be designed to withstand very large forces in a small, compact package.

Hip Actuator Hydraulics

Figure 8:
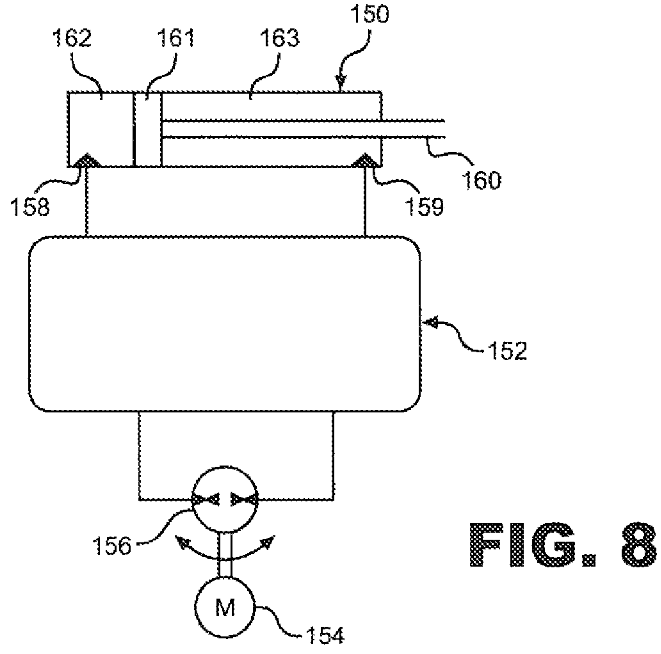
FIG. 8 is a diagram of a hydraulic circuit connected to a non-symmetrical linear hydraulic hip actuator of the present invention.

In accordance with the preferred embodiment, linear actuator 110 is in the form of a hydraulic actuator 150 and controller 108 is in the form of a hydraulic circuit 152 as depicted in FIG. 8. When electric power is provided by power source 109 to an electric motor 154, electric motor 154 drives a hydraulic pump 156 that moves and pressurizes hydraulic fluid within hydraulic fluid circuit 152. The hydraulic fluid is routed through hydraulic circuit 152 to hydraulic hip actuator 150 and allows hydraulic hip actuator 150 to create mechanical force and motion to move orthotic hip joint 103. In one embodiment, hydraulic actuator 150 is a non-symmetrical actuator including a first fluid port indicated at 158 and a second fluid port indicated at 159. Fluid pressure within hydraulic actuator 150 caused by fluid flowing from hydraulic circuit 152 into hydraulic actuator 150 through first port 158 causes movement of an actuator rod 160 attached to a piston 161 in as first direction, while fluid pressure within hydraulic actuator 150 caused by fluid flowing from hydraulic circuit 152 into hydraulic actuator 150 through second port 159 causes movement of piston 161 in a second direction. The location of piston 161 within hydraulic actuator 150 dictates the volume of first and second fluid chambers 162 and 163 in a manner known in the art. As previously discussed, piston 161 is preferably connected to mechanical transmission mechanism 111 and the movement of piston 161 causes movement of mechanical transmission mechanism 111 to cause flexion or extension of thigh link 101 relative to hip link 102. For the sake, of completeness, examples of electric motor 154 include, without limitation, AC (alternating current) motors, brush-type DC (direct current) motors, brushless DC motors, electronically commutated motors (ECMs), and combinations thereof, while examples of hydraulic pump 156 include, without limitation, internal gear pumps, external gear pumps, axial piston pumps, rotary piston pumps, vane-type pumps, and combinations thereof.

Figure 9:
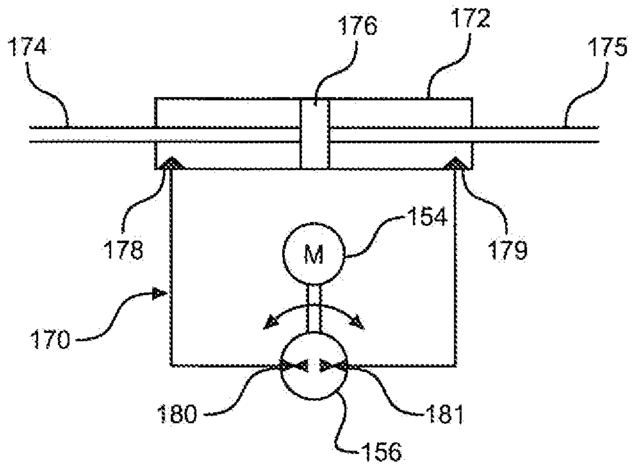
FIG. 9 is a diagram of a hydraulic circuit connected to a symmetrical linear hydraulic hip actuator of the present invention.

FIG. 9 shows a simple example of a hydraulic circuit 170 which can be employed in the present invention. This example can be used when linear actuator 110 is in the form of a symmetric hydraulic actuator indicated at 172, such as a double-rod, double-acting linear actuator or a hydraulic rotary actuator. Here, a double-rod actuator 172 is shown including actuator rods 174 and 175 connected to a common piston 176. In symmetric hydraulic actuator 172, the same flow of hydraulic fluid exits one of the actuator's hydraulic ports 178, 179 as enters the actuator's other hydraulic port 179, 178. Because of this symmetry, hydraulic circuit 170 is reduced to a direct connection of the ports of hydraulic pump 156 indicated at 180 and 181, to ports 178 and 179 of symmetric hydraulic actuator 172.

Figure 10:
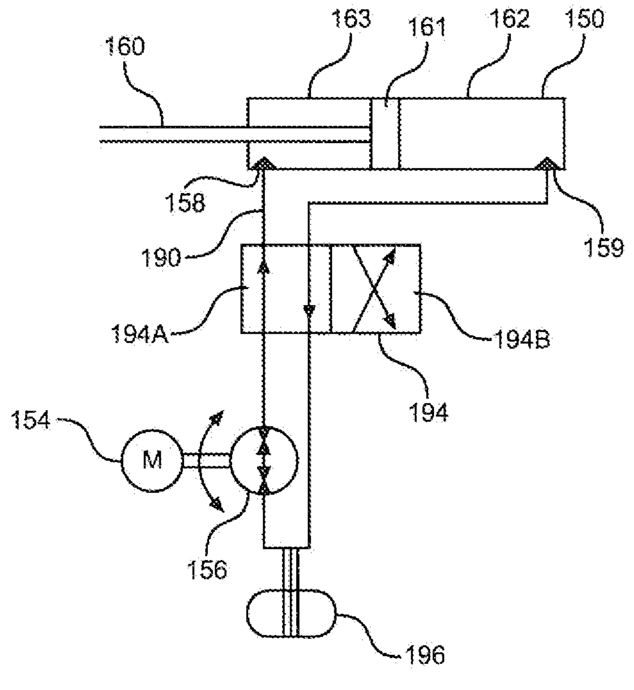
FIG. 10 is a diagram of a hydraulic circuit including a reversing valve connected to the non-symmetrical linear hydraulic hip actuator.

FIG. 10 depicts a hydraulic circuit 190 for use with a non symmetric hydraulic linear actuator 150. For non-symmetric hydraulic actuators, such as single-rod double-acting linear actuators also corresponding to that of FIG. 8, the associated hydraulic circuit is more complicated due to the fact that the actuator's two ports have different flows. As depicted in FIG. 10, hydraulic pump 156 always runs in the same direction and a reversing hydraulic valve 194 controls which actuator port 158 or 159 sees that pressure. The actuator port, not receiving hydraulic fluid is connected a reservoir 196 that also connects to the low pressure side of pump 156. Reversing hydraulic valve 194 is depicted as having two configurations, 194A and 194B. As depicted, with valve 194 in configuration 194A, electric motor 154 creates a force functioning to retract rod 160 through piston 161 of hydraulic actuator 150. Hydraulic valve 194 needs to be actively switched to its other configuration 194B before rod 160 of hydraulic actuator 150 can be forced to extend. The port 158 or 159 not connected to hydraulic pump 156 is connected to hydraulic reservoir 196. Since a non-symmetric hydraulic actuator contains different volumes of fluid depending on its position, hydraulic reservoir 196 stores excess hydraulic fluid allowing the volume of fluid in actuator 150 to change as desired. Hydraulic, valve 194 must be switched whenever the desired actuation torque switches direction.

FIG. 11 illustrates an alternative hydraulic circuit 200 for non-symmetric hydraulic actuators 150 that do not require active switching of a hydraulic valve. More specifically, two pilot check valves 202 and 203 allow fluid to flow in and out of reservoir 196 as necessary, while still allowing hydraulic pump 156 to push hydraulic fluid into hydraulic hip actuator 150. Pilot check valve 202 acts as a one-way valve when there is no pressure in its pilot passage or port 206 and allows free fluid movement in both directions when there is pressure in pilot passage 206. When it is desired to force rod 160 to retract, electric motor 154 turns hydraulic pump; 156 in the direction to force fluid right to left through pump 156. This creates a pressure on the left side of pump 156 and, therefore, in a pilot passage 267 which causes right pilot check valve 203 to be forced open. Since there is higher fluid flow in the right port 159 of hydraulic hip actuator 150 than the left port 158, forcing the right pilot check valve 203 open gives a path for extra fluid to enter reservoir 196. Without pilot check valves 202 and 203, there would be no way to get the extra actuator fluid into reservoir 196 as the actuator rod 160 associated with piston 161 retracts. In this configuration, hydraulic pump 156 runs in different directions depending on whether single-rod hydraulic actuator 150 is extending or retracting. However, pump 156 needs to turn at a different rate in order to extend rod 160 than to retract rod 160 at the same speed. For example, when moving piston 161 and rod 160 of hydraulic hip actuator 150 in FIG. 11 to the right one inch (retracting), pump 156 needs to pump less fluid than when moving piston 160 of hydraulic hip actuator 150 to the left one inch (extending). This means that hydraulic circuit 200 shown in FIG. 11 has a different effective gear ratio in one direction than the other. Applying this circuit to orthotic device 100 of the present invention is advantageous because it allows the engineer to more easily optimize the size of motor 154. The reason for this is that orthotic hips (like human hips) require fast motion at low torque during swing and slower motion at high torque during stance. By allowing a designer to effectively establish a different gear ratio in the swing direction versus the stance direction, this circuit allows one to optimize the design for low weight and high efficiency more easily than the double-rod actuator circuit shown in FIG. 9. Moreover, it can, switch directions more rapidly and more easily than the circuit shown in FIG. 10, while also eliminating the need, to control a valve.

FIG. 11 illustrates a hydraulic circuit 200 that operates properly when hydraulic hip, actuator 150 is providing positive power (force and movement in the same direction) and negative power (force and movement opposing each other) to hip joint 103. FIG. 12 illustrates an alternative hydraulic circuit 220 which, utilizes only one pilot check valve 203 in the case where hydraulic hip actuator 150 is only used in positive power operations. In FIG. 12, hydraulic hip actuator 150 is not capable of providing negative power in the direction of piston motion to the right in the figure. It cannot do this because it cannot attain a high pressure on the right side of the cylinder while it is being pushed by an external force to the right. In this configuration, the piloted check valve 202 of the configuration depicted in FIG. 11 is replaced, with a standard check valve 224. In this case, if one were to try to force piston 161 of hydraulic hip actuator 150 to the right using an external force, a large quantity of fluid would exit the right hand port 159, and pressure would tend to rise on the right hand side of the circuit, however, the fluid cannot initially pass piloted check valve 203. For this reason the fluid passes through pump 156 in the direction to the left in the figure. The volume is increasing on, the left hand side 163 of piston 161 in hydraulic actuator 150, but not at a rate high enough to receive all of the fluid from fluid chamber 162 on the right hand side of piston 161 (which has a larger cross section). This means that the pressure in all of hydraulic circuit 220 which is on the "pump side" of check valves 203 and 224 will rise in pressure. The pressure, however, will only increase until a pilot passage 226 has reached the "cracking pressure" of the piloted check valve 203, at which point piloted check valve 203 will open, and the pressure will start to drop as fluid escapes into reservoir 196. When the pressure has dropped below the "cracking pressure," piloted check valve 203 will close again and pressure starts to build. This circuit therefore will, produce an oscillatory, pressure when piston 161 of hydraulic actuator 150 is pushed to the right by an external force and this oscillatory pressure will not be higher than the "cracking pressure" of piloted check valve 203. The circuit 220, therefore, cannot be used to resist such motion to the right at an arbitrary pressure.

Hip and Knee Combined Hydraulics

When powered leg orthotic device 100 also contains a hydraulic knee torque generator 107, a common hydraulic circuit with pump and motor can be employed for common control or a second hydraulic circuit, hydraulic pump, and electric motor similar to FIGS. 9-12 can be added to independently control the orthotic's knee motion and torques. Certainly, the overall system is lighter weight and more compact if hip torque generator 106 and knee torque generator 107 share the same hydraulic pump 156 and electric motor 154. Whichever hydraulic circuit is used, the requirements for knee torque generator 107 are different from those of hip torque generator 106 since knee torque generator 107 needs to be able to produce very high resistance to motion during heel strike and very low resistance to motion during free, passive swing. It is also desirable for knee torque generator 107 to be actively actuated in the extension direction during stance when climbing a slope or a stair.

Figure 13:
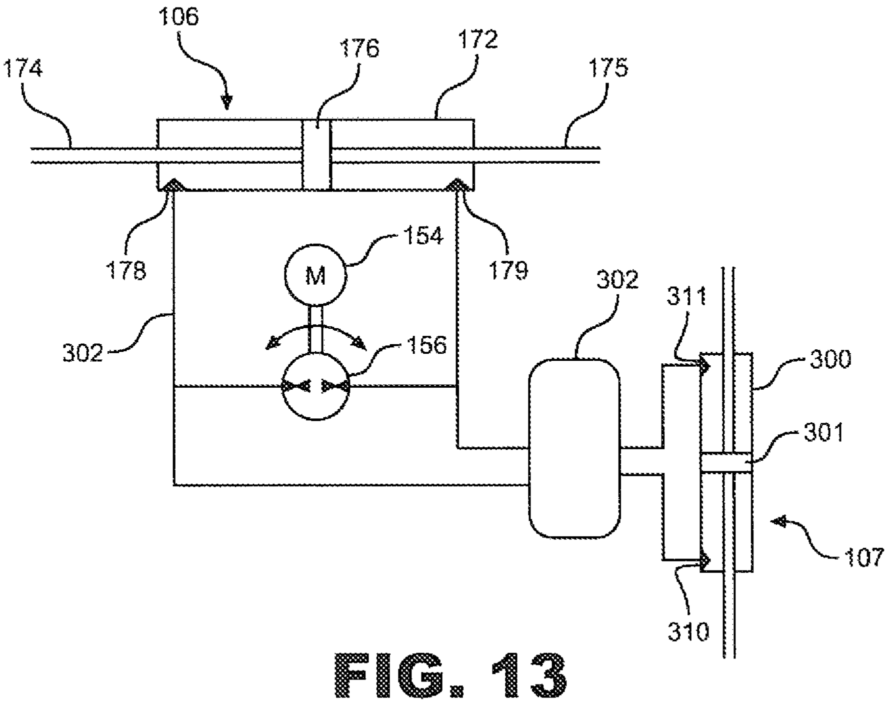
FIG. 13 is a diagram of a hydraulic circuit connecting the symmetrical linear hydraulic hip actuator to a symmetrical linear hydraulic knee actuator through a hydraulic valve.
Figure 14:
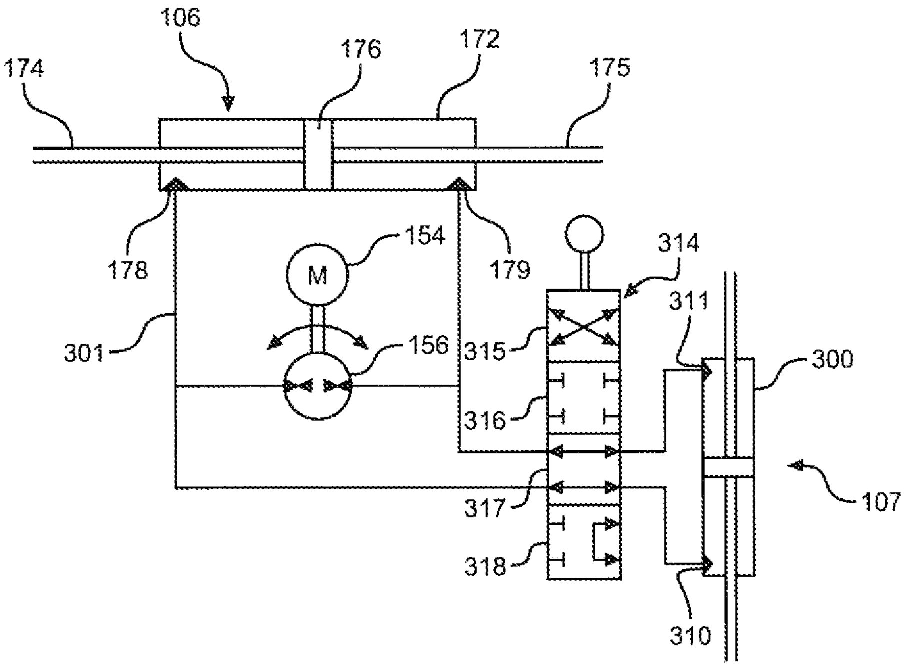
FIG. 14 is a diagram of the hydraulic circuit of FIG. 13, where the hydraulic valve is a four position hydraulic valve.

In one preferred embodiment, knee actuator 107 is in the form of a symmetric hydraulic actuator 300 including a piston 301. FIG. 13 illustrates a hydraulic circuit 302 using one hydraulic pump 150 and electric motor 154 to power both hydraulic knee actuator 107 and hydraulic hip actuator 106 in the case where actuators 107 and 106 are both symmetric actuators. A hydraulic valve 302 is used to either connect knee actuator 107 to pump 156 or to fluidly connect ports 310 and 311 of hydraulic knee actuator 300 together. Valve 302 can be configured to connect ports 310 and 311 of hydraulic knee actuator 300 together with a varying amount of resistance from zero to infinity. FIG. 14 illustrates one embodiment of hydraulic valve 302 to accomplish this. In this case, hydraulic valve 302 is in the form of a four position hydraulic valve 314. Valve 314 is schematically shown for each of its four positions. In a first position indicated at 315, port 311 of hydraulic knee actuator 300 is in communication with port 178 of hydraulic, hip actuator 172 and port 310 of hydraulic knee actuator 300 is in communication with port 179 of hydraulic hip actuator 172. In a second position indicated at 316, all ports of valve 314 are blocked. In a third position indicated at 317, port 311 is in communication with port 179 and port 310 is in communication with port 178. Finally, in the fourth position indicated at 318, ports 310 and 311 of knee actuator 300 are in fluid communication with each other, but not with hydraulic hip actuator 172. Note that pressure which can be provided by pump 156 to hydraulic knee actuator 300 always is equal to or less than the pressure provided to hydraulic hip actuator 172. Therefore, care must be taken. When designing the actuation such that the desired hip and knee torques can always be achieved.

Figure 15:
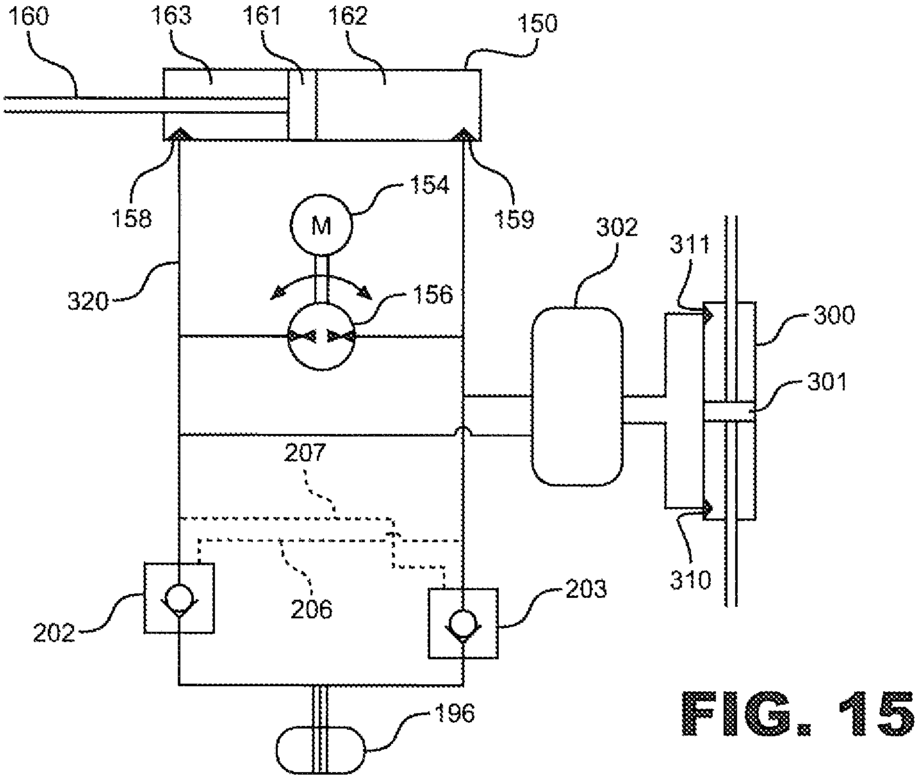
FIG. 15 is a diagram of a hydraulic circuit including first and second pilot check valves connecting the non-symmetrical linear hydraulic hip actuator to the symmetric linear hydraulic knee actuator through a hydraulic valve.
Figure 16:
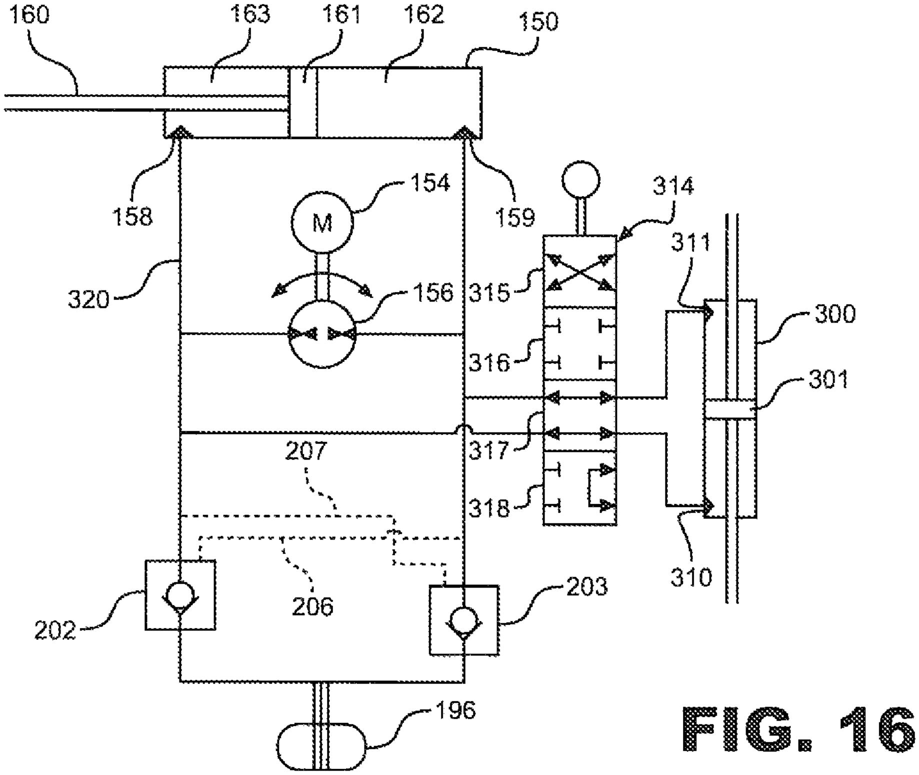
FIG. 16 is a diagram of the hydraulic circuit of FIG. 15, where the hydraulic valve is a four position hydraulic valve.
Figure 17:
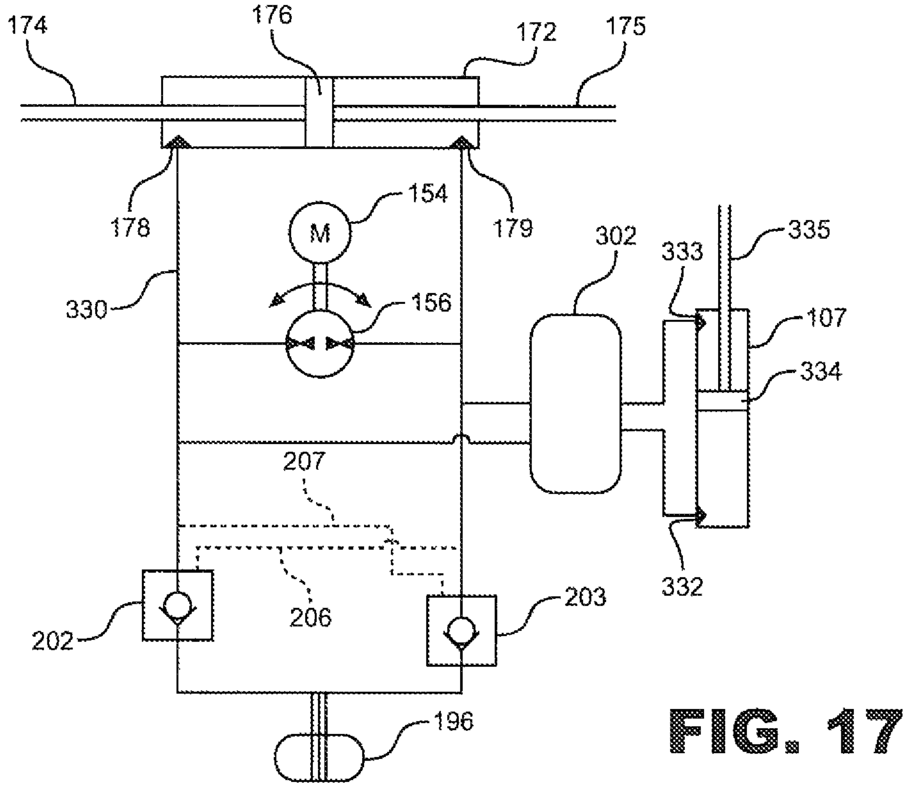
FIG. 17 is a diagram of a hydraulic circuit including first and second pilot check valves connecting the symmetrical linear hydraulic hip actuator to the non-symmetric linear hydraulic knee actuator through a hydraulic valve.
Figure 18:
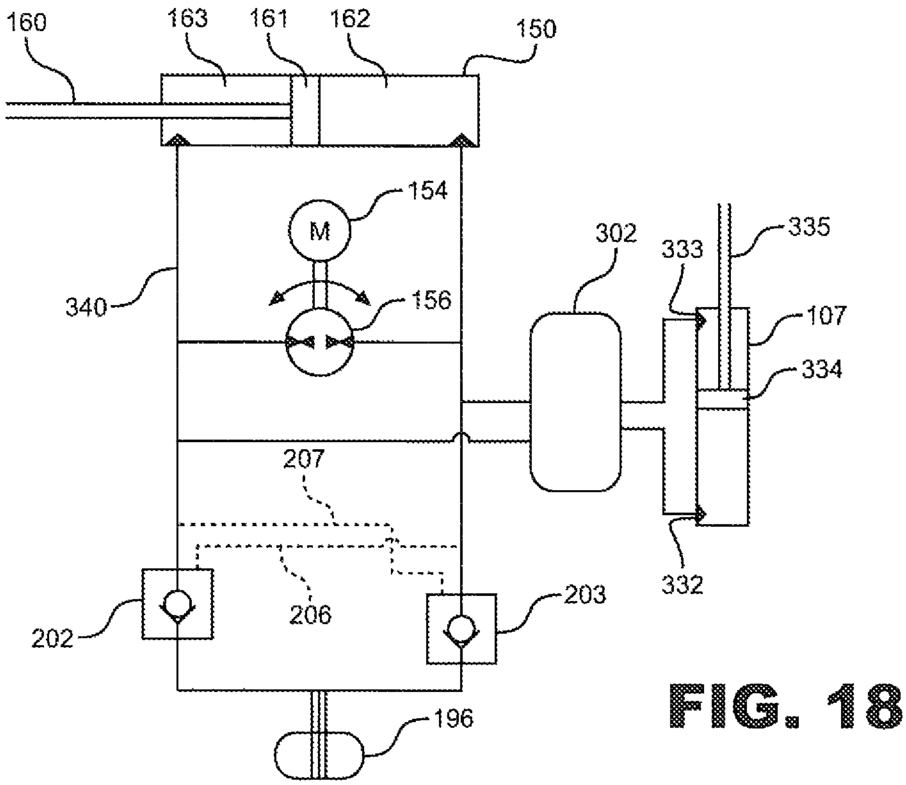
FIG. 18 is a diagram of a hydraulic circuit including first and second pilot check valves connecting the non-symmetrical linear hydraulic hip actuator to the non-symmetric linear hydraulic knee actuator through a hydraulic valve.

The hydraulic circuit of the present invention becomes more complicated whenever either the hip or knee actuator 106, 107 is non-symmetric (stick single-rod hydraulic cylinders). Either another hydraulic valve or pilot check valves can be added to handle the mismatched flows of non-symmetric actuators (such as described for FIGS. 10 and 11). FIG. 15 illustrates a hydraulic circuit 320 for a non-symmetric hydraulic hip actuator 150 using pilot check valves 202 and 203. Circuit 320 in this portion of the figure is the equivalent to circuit 200 of FIG. 11, except that circuit 320 communicates through hydraulic valve 302 with hydraulic knee actuator 300. FIG. 16 is the same figure as FIG. 15, except that it shows an embodiment wherein hydraulic valve 302 is in the form of four position hydraulic valve 314. The valve configuration is schematically shown for each of the positions. An alternative hydraulic circuit 330 is depicted in FIG. 17 for use with a symmetric hip actuator 172 and non-symmetric knee actuator 107. Non-symmetric knee actuator 107 includes ports 332 and 333 as well as a piston 334 and a piston rod 335. Another alternative hydraulic circuit 340 is depicted in FIG. 18 for use with non-symmetric hip actuator 150 and non-symmetric knee actuator 107.

Figure 19:
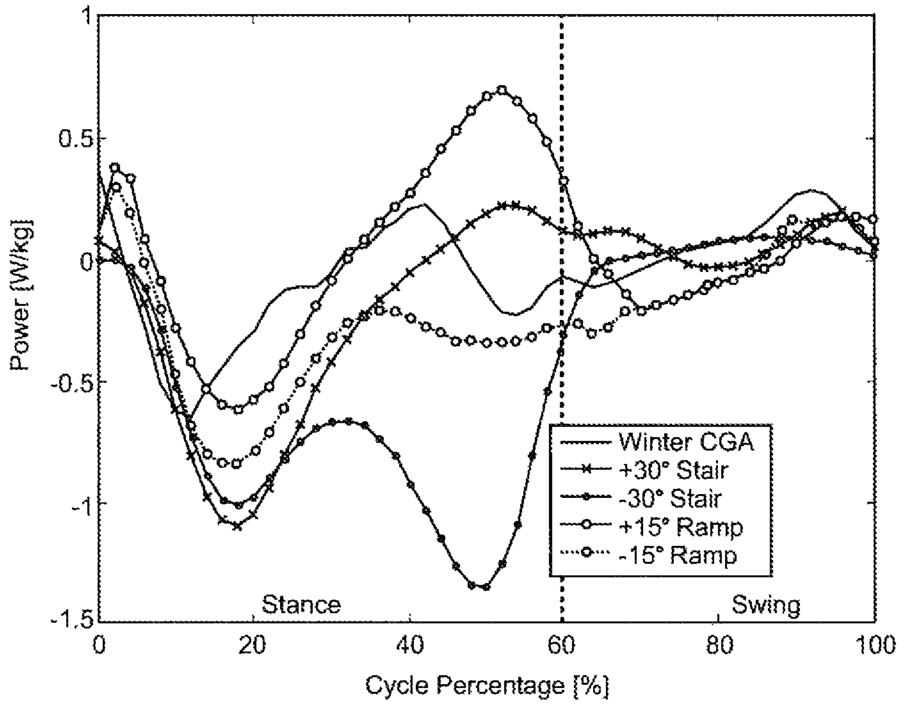
FIG. 19 illustrates torques generated by a human knee during various walking cycles.
Figure 20:
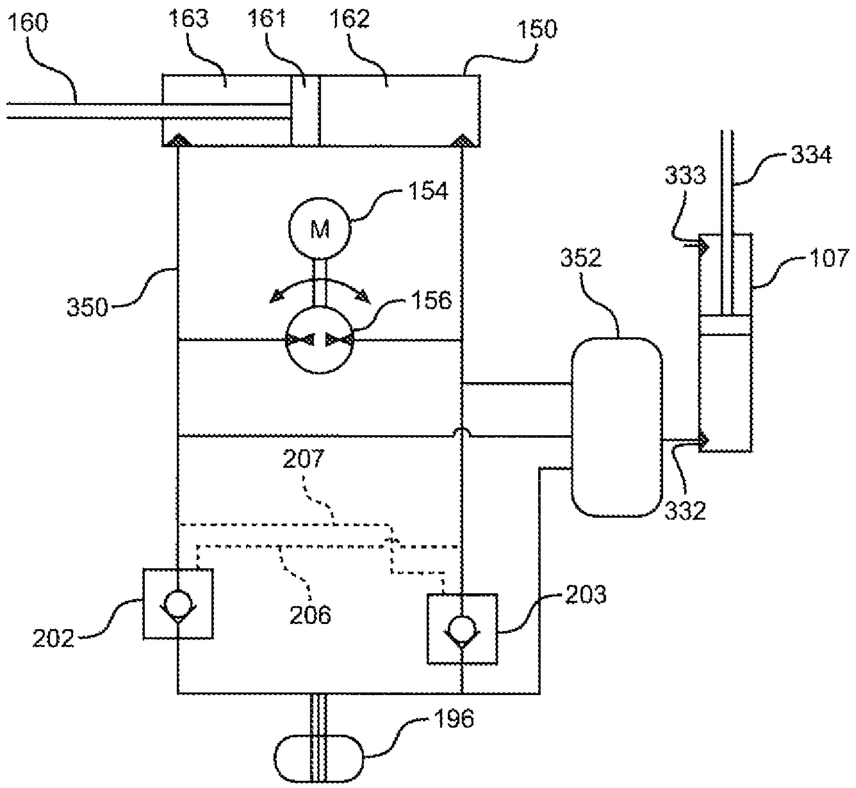
FIG. 20 is a diagram of a hydraulic circuit including first and second pilot check valves connecting the non-symmetrical linear hydraulic hip actuator to a single port of the non-symmetric linear hydraulic knee actuator through a hydraulic valve.

A study of human knee torques derived from clinical gait analysis reveals that the only large torques generated at the knee are in the extension direction (see FIG. 19). Therefore, a simpler hydraulic circuit was developed that takes advantage of the fact that the knee can be single acting and only capable of providing an extension force/torque. FIG. 20 depicts a hydraulic circuit 350 where hydraulic hip actuator 150 is non-symmetric and hydraulic knee actuator 107 is a single-acting actuator. Here, a hydraulic, valve 352 allows knee actuator 107 to be powered whichever way hydraulic pump 156 is moving. Hydraulic valve 352 can also connect knee actuator 107 to reservoir 196 with a varying resistance from zero to infinity.

Figure 21:
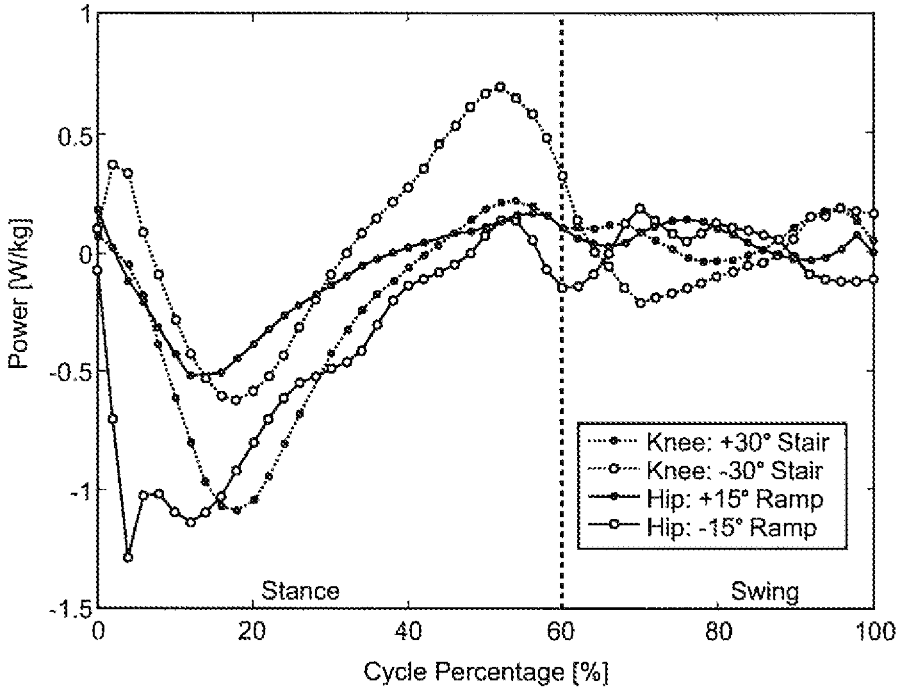
FIG. 21 illustrates typical human knee and hip torques generated during the climbing of stairs and ramps.
Figure 22:
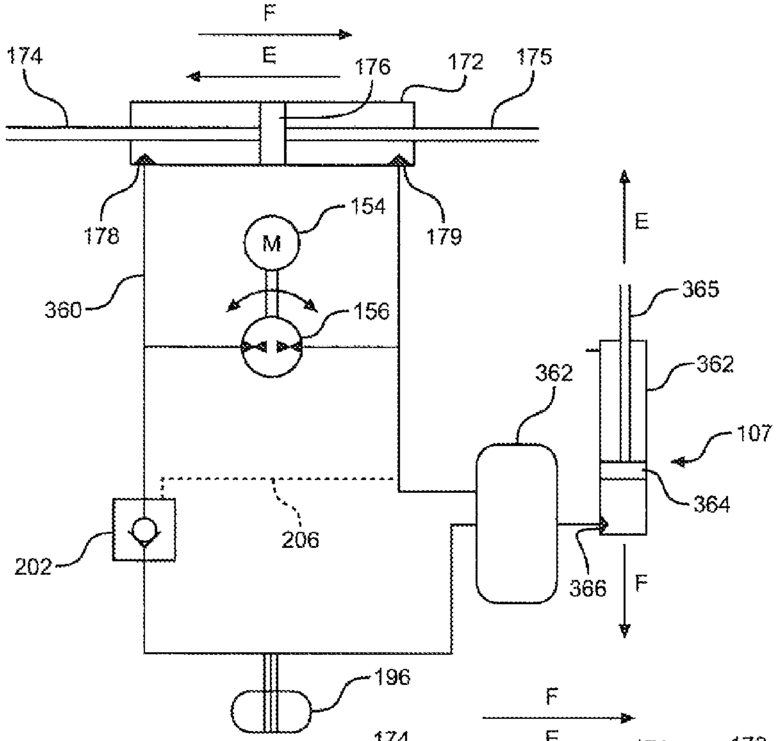
FIG. 22 is a diagram of a hydraulic circuit including first and second pilot check valves connecting the symmetrical linear hydraulic hip actuator to a single port of the non-symmetric linear hydraulic knee actuator through a hydraulic valve.

FIG. 21 compares typical human knee and hip torques generated by clinical gait analysis for various high powered movements such as climbing stairs and ramps. Notice how the hip and knee torques generally are in the same direction. A further hydraulic simplification was developed in the case where knee actuator 107 can only be extended while the hip of a user is being extended. FIG. 22 illustrates this alternative hydraulic circuit 360 connecting symmetric hydraulic hip actuator 172 to a single-acting knee adulator 362 that is only powered when the hip of a user is being extended. As seen in FIG. 22, single-acting knee actuator 362 includes a piston 364 and rod 365, as well as a single hydraulic fluid port 366. The direction of movement of rods 174 and 175 in hydraulic hip actuator 172 during extension is shown by the arrow E in FIG. 22. A left pilot check valve 202 is utilized for reasons that will be explained below with reference to FIG. 23.

Figure 23:
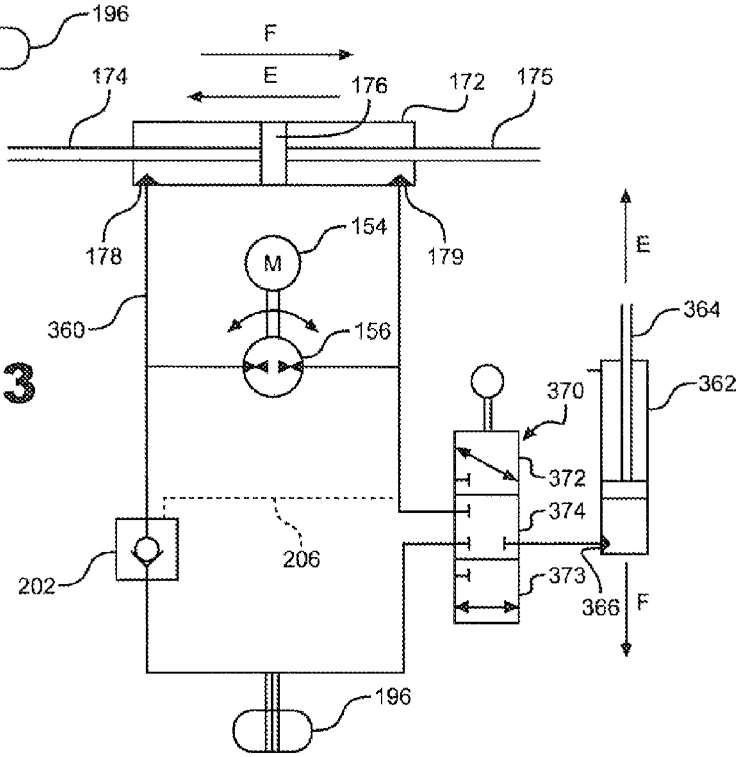
FIG. 23 is a diagram of the hydraulic circuit of FIG. 22, where the hydraulic valve is a three-position valve.

FIG. 23 illustrates the hydraulic circuit 360 of FIG. 22 wherein a hydraulic valve 362 is in the form of a three-position hydraulic valve 370. The three position hydraulic valve 370 can connect knee actuator 362 to hydraulic pump 156 for extension, as indicated by a first valve position 372, or to the reservoir 196 as indicated by a bottom valve position 373. Valve 370 can also be utilized in a center position indicated at 374, wherein all valve ports are blocked to provide full resistance to knee flexion. To provide an adjustable passive resistance to flexion, valve 370 can operate between the middle state 374 where all ports are blocked and the bottom position 373, where knee actuator 362 is connected to reservoir 196. To provide only part of the pressure being supplied to hydraulic hip actuator 172 to hydraulic knee actuator 362, valve 370 can be operated between its top and middle positions 370 and 374. This valve embodiment is noticeably simpler than previously required valves. Now, it can be seen clearly why piloted check valve 202 is utilized in this circuit. If valve 370 is operating in its top position 372 (with hydraulic knee actuator 362 connected to pump 156), and an external force is pushing hydraulic knee actuator 362 in the direction of flexion indicated at arrow F, pressure will build in pilot passage 206 and pilot check valve 202 will open, providing a path (through pump 156) for fluid to move out of the hydraulic knee cylinder 362. This allows the user of the orthotic device more freedom by allowing force flexion of the knee to occur while pump 156 is providing extension pressure to both cylinders.

Figure 24:
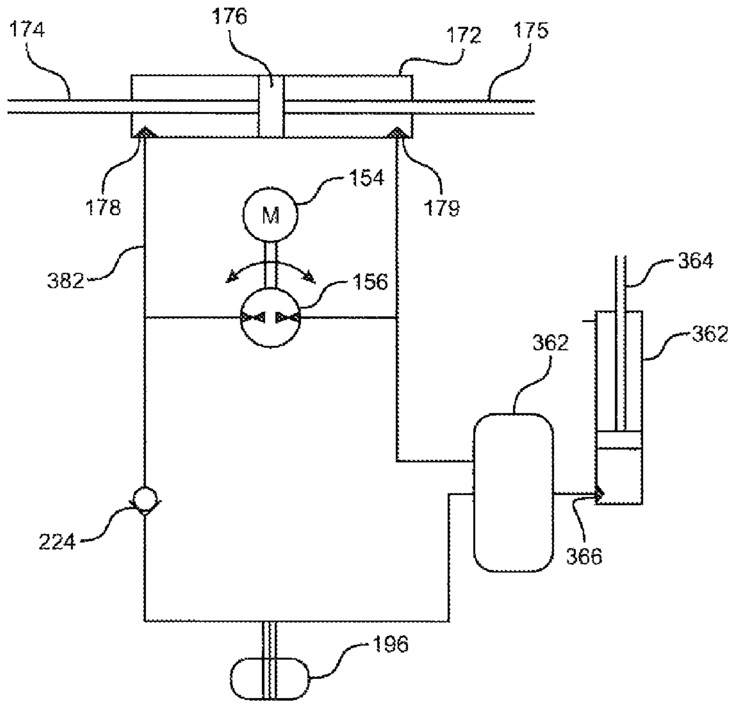
FIG. 24 is a diagram of a hydraulic circuit including one pilot check valve connecting the symmetric linear hydraulic hip actuator to a single port of the non-symmetrical linear hydraulic knee actuator through a hydraulic valve.

The hydraulic circuit is simplified slightly more if knee actuator 362 is only operated in positive power situations. In this case, the pilot check valve 202 of FIG. 23 is replaced with a standard check valve 224 as seen in the alternative hydraulic circuit 382 depicted in FIG. 24.

Figure 25:
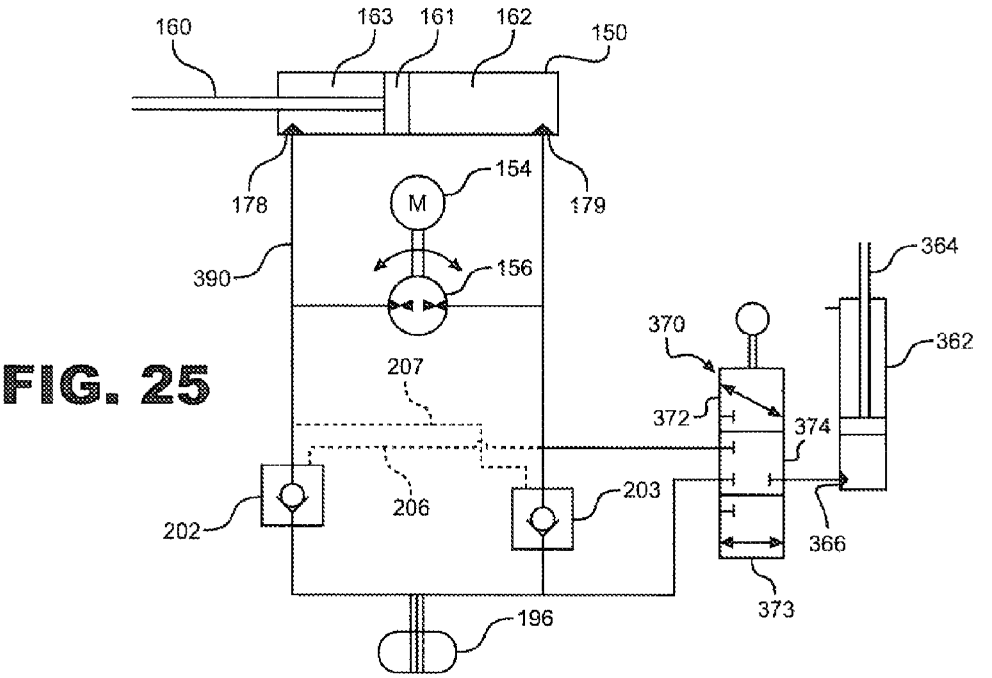
FIG. 25 is a diagram of the hydraulic circuit of FIG. 24, where the hydraulic valve is a three-position valve.

FIG. 25 illustrates a case where hydraulic hip actuator 150 is anon-symmetric hip actuator combined with, the case where hydraulic knee actuator 362 is a single acting actuator. The same valve embodiment can be used as seen in FIG. 23, but both pilot check valves 202 and 203 are employed for the non-symmetric hip actuator 362 to operate properly. This circuit 390 combines the advantages, of non-symmetric hip actuator 150 (as described previously) with the advantages of single acting knee actuator 362, which eliminates at least one hydraulic line and associated components.

Figure 26:
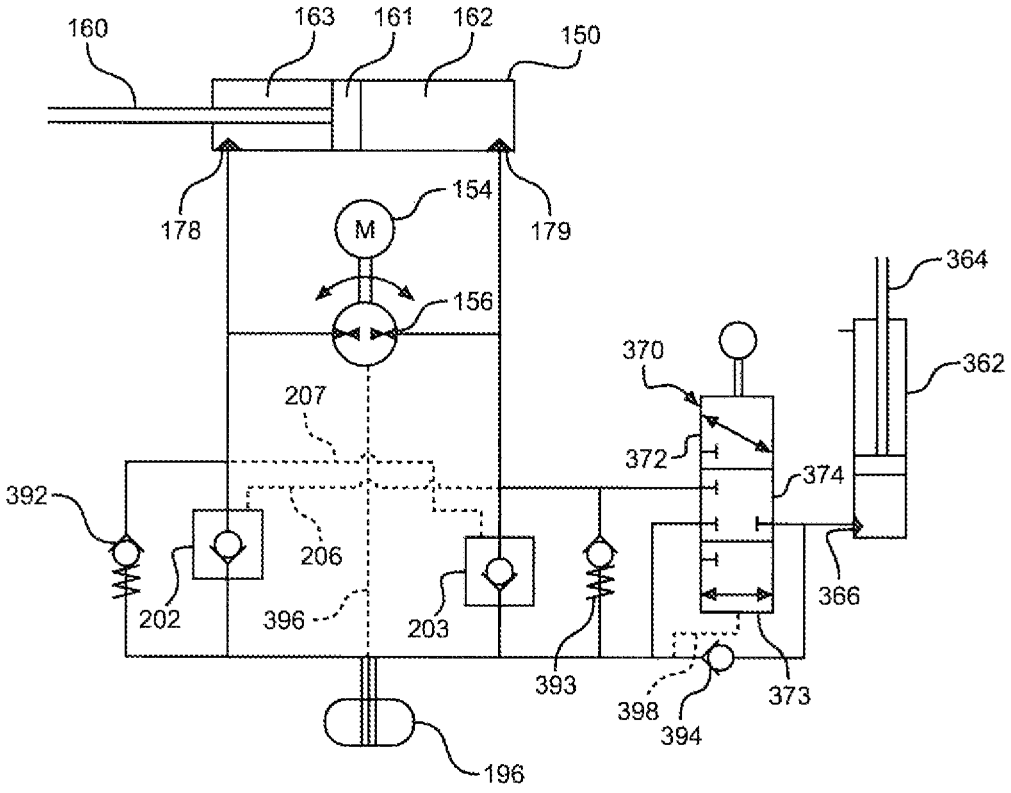
FIG. 26 is a diagram of the hydraulic circuit of FIG. 25, including three pressure relief valves.

FIG. 26 shows an implemented embodiment of FIG. 25 with additional details of the hydraulic system. Pressure relief valves 392 and 393 have been added to prevent over-pressurizing the system. A pump drain path 396 provides a leak path from the housing of pump 156 to reservoir 196. This leak path 396 is used for lubricating components of pump 156 by being routed through the bearings of the moving components within pump 156. A valve drain path 398 provides a leak path from the housing of valve 370 to reservoir 196 and ensures that high pressure does not build up around the body of valve 370, which would increase the power necessary to move valve. Knee extension cheek valve 394 is provided for safety. More specifically, valve 394 ensures that a user of the orthotic device 100 can always extend their knee in the case that they are stumbling. Based on the above discussion of various preferred embodiments, it should be clear that the hip and knee torque generators synergistically operate to provide for a natural walking motion with the electric motor providing energy for the orthotic device without the need for any additional energy dissipating device between the motor and the hip and knee actuators. Instead, during normal use, the knee actuator can act as an energy dissipating device.

Hip Layout

The implementation of hip torque generator 106 can take on a variety of different embodiments. While the mechanical transmission mechanism 111 is typically interposed for hip joint 103, depending on the selected embodiment of the hip actuator 110 and specific mechanical transmission mechanism 111, the position of the rest of the actuation is highly variable. Using the preferred embodiment of a four-bar mechanism 120, linear hydraulic actuator 150, hydraulic circuit 390 from FIG. 26, a hydraulic pump 156, and electric motor 154, FIG. 27 illustrates a novel layout that solves many of the problems encountered when designing a powered hip orthotic.

Figure 27:
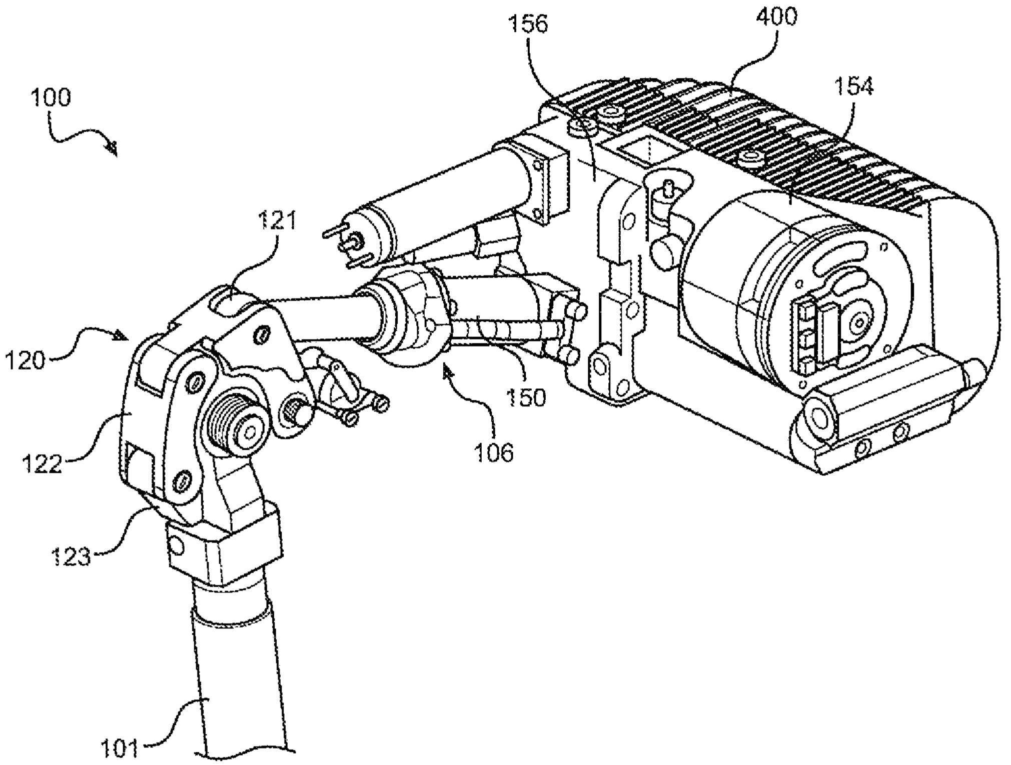
FIG. 27 is a partial perspective view of one embodiment of the lower limb orthotic device of the present invention.
Figure 28:
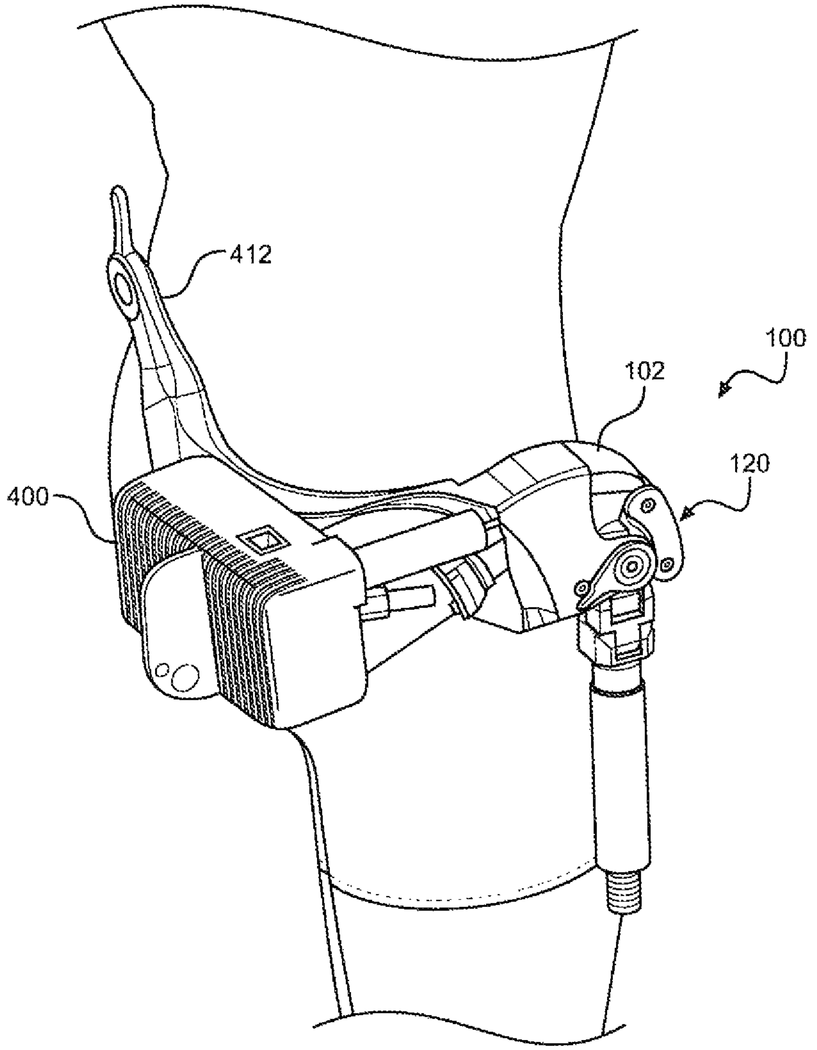
FIG. 28 is a partial perspective view of the lower limb orthotic device of FIG. 27 worn by a person.

The preferred layout of FIG. 27 has several advantages. The first is that it can create a powered hip orthotic 100 which is very narrow when viewed from the front of the user. The user's orientation can be seen in FIG. 28. The four-bar mechanism 120 and linear hydraulic actuator 150 can be packaged close to the user's hip joint in a very minimal width away from the user. With the relatively narrow four-bar mechanism 120 and linear hydraulic actuator 150 placed next to the user, powered orthotic 100 is not significantly wider than the user's, hips. The larger electric motor 154, hydraulic pump 156 and hydraulic circuit are then placed behind the user's back, yielding an arrangement that naturally curves close to and around the user's hips. FIG. 28 illustrates this preferred layout mounted to a structural orthotic hip link 102 and depicted around a user's hips. Another advantage of this layout is that it eliminates the use of flexible hydraulic lines to connect pump 156 to actuator 150. It does this by placing both pump 156 and actuator 150 on hip link 192. Hip link 102 establishes an advantageous, position for these elements because it does not move very much during regular walking. Therefore, increasing the inertia of link 102 (as opposed to thigh link 101 for example) does not have much impact on torques required by the orthotic hip device 100. With this layout, a heat sink 400 for motor 154 and pump 156 is also located behind the user in order to allow for heat dissipation with minimum effect on the user.

Figure 29:
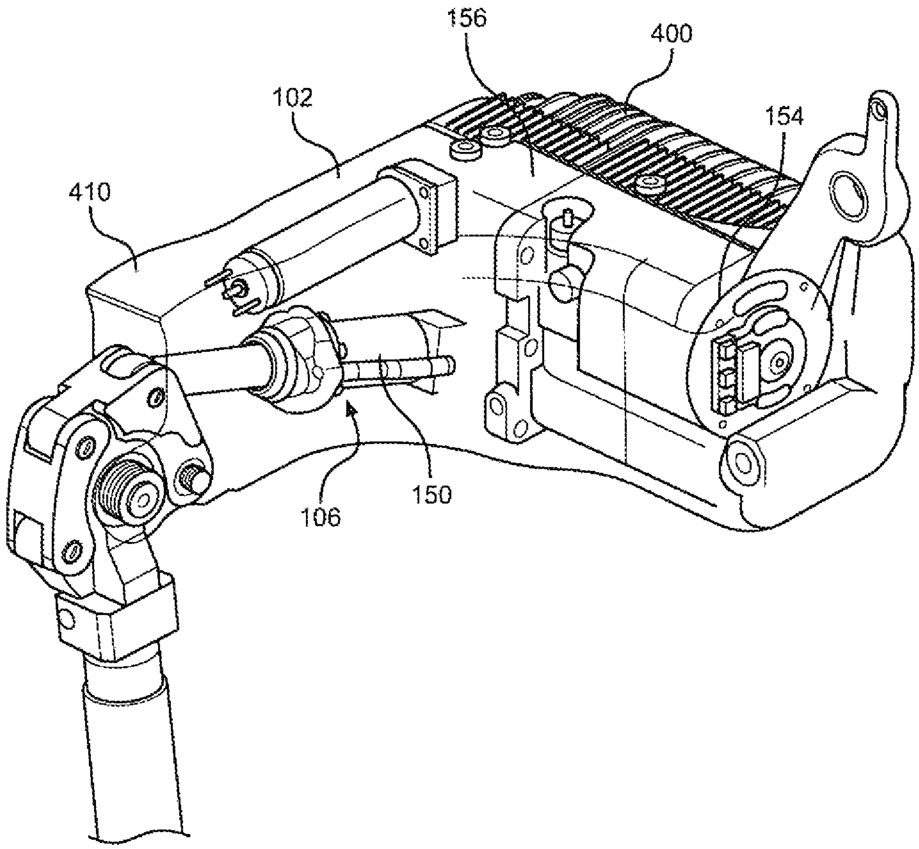
FIG. 29 is a partial perspective view of an alternative embodiment of the lower limb orthotic device of the present invention.

Because of the tight compact nature of this preferred embodiment, an alternative, to mounting hip torque generator 106 to an open hip link, such as hip link 102 shown in FIG. 28, is to mount hip torque generator 106 inside hip link 102 as seen in FIG. 29. This allows the mechanism to be protected by a thin walled structure or housing 410 which can also transmit large forces transferred through an orthotic leg device 100 up to a torso of an orthotic device (not shown), which could be connected at a hip abduction/adduction pivot 412 depicted in FIG. 28.

It is important to note also that pump 156 and motor 155 are mounted orthogonally to the axis of the hip hydraulic actuator 150. This allows the hip assembly to retain a center of gravity which is much closer to the person than the if the motor 154 and pump 156 were mounted in the same line as hip hydraulic actuator 150. Mounting the pump 156 and motor 154 horizontally was selected in this embodiment in order to interfere the least with a load carried behind the user by the orthotic.

Although described with reference to preferred embodiments of the invention, it should be readily understood that various changes and/or modifications can be made to the invention without departing from the spirit thereof. For instance, motor 154 and pump 156 can be mounted orthogonally to hip hydraulic actuator 150 in a different manner by mounting them with their axes of rotation vertical instead of horizontal. In general, the invention is only intended to be limited by the scope of the following claims.

The invention claimed is:

1. A lower limb orthotic device adapted to be worn by a user comprising:

a thigh link adapted to couple to a user's lower limb;

a hip link;

a hip joint rotatably coupling the thigh link and the hip link to allow flexion and extension between the thigh link and the hip link through a range of motion;

a power source; and a hip torque generator interconnected between the thigh link and the hip link, the hip torque generator including:

a hip actuator; and a mechanical transmission mechanism connected to the hip actuator, wherein the mechanical transmission mechanism includes a multi-bar linkage having at least first, second and third pivoting links, with the hip actuator and the mechanical transmission mechanism being interposed between the thigh link and the hip link;

a fluid circuit fluidly connected to the hip actuator;

a pump adapted to develop a flow of fluid in the fluid circuit; and an electric motor for applying torque to the pump, wherein the pump is in direct communication with the fluid circuit such that torque applied to the hip joint is regulated by controlling a torque applied to the pump through the electric motor.

2. The orthotic device of claim 1, wherein the mechanical transmission mechanism further includes a fourth link, said fourth link establishing a fixed pivot axis for the hip joint.

3. The orthotic device of claim 1, wherein the hip actuator constitutes a non-symmetric linear actuator including a piston connected to a rod.

4. The orthotic device of claim 3, wherein the non-symmetric linear actuator includes first and second fluid ports positioned on opposing sides of the piston and in communication with the fluid circuit, and wherein the fluid circuit includes at least a first check valve regulating the flow of fluid from the first fluid port to the second fluid port and a fluid reservoir adapted to be placed in fluid communication with the first and second fluid ports.

5. The orthotic device of claim 4, wherein the at least one check valve is a pilot check valve, said fluid circuit providing multiple effective gear ratios such that the pump turns at a first rate in order to extend the rod and at a second rate in order to retract the rod at the same speed, and wherein the multiple effective gear ratios provides for a first motion at a first torque during a swing phase of the orthotic device and a second motion at second torque during a stance phase of the orthotic device, wherein the second motion is slower than the first motion and the second torque is higher than the first torque.

6. The orthotic device of claim 1, wherein the hip actuator constitutes a symmetric linear actuator including a single piston and opposing rods.

7. The orthotic device of claim 1 wherein, with the direct communication between the pump and the fluid circuit, operation of the pump in a first direction produces flexion in the hip joint and operation of the pump in a second, opposite direction produces extension in the hip joint.

8. The orthotic device of claim 1, further comprising: a shank link adapted to be coupled to a user's lower limb, said shank link being rotatably coupled to the thigh link via a knee joint.

9. The orthotic device of claim 8, further comprising:

a knee torque generator coupled to the thigh link and the shank link, the knee torque generator including:

a knee actuator; and a mechanical transmission mechanism connecting the knee actuator to the shank link; and a valve located between the knee actuator and the fluid circuit to regulate a flow of fluid, generated by operation of the motor and pump which is common to the hip torque actuator, between the knee actuator and the fluid circuit.

10. The orthotic device of claim 9, wherein the knee actuator is a non-symmetrical linear actuator.

11. The orthotic device of claim 9, wherein when the valve located between the knee actuator and the fluid circuit connects the knee actuator to the fluid circuit and the pump is operated in a direction which applies the torque to the hip joint in a direction which acts to cause hip extension, a torque will result in the knee actuator, due to fluid pressure from the fluid circuit, which applies a torque to the knee joint in a direction which acts to cause knee extension.

12. The orthotic device of claim 11, wherein the hip and knee actuators are sized such that a ratio of hip extension torque produced to knee extension torque produced corresponds to a ratio present in humans during ascension of stairs and steep slopes.

13. The orthotic device of claim 9, wherein the valve is a three-position valve allowing the fluid communication from the fluid circuit to the knee actuator in a first position, fluid communication from the knee actuator in a second position; and blocking fluid communication between the fluid circuit and the knee actuator to resist flexion of the knee actuator in a third position.

14. The orthotic device of claim 9, wherein the valve is a four-position valve allowing fluid communication between a first port of the knee actuator and a second port of the hip actuator and between a second port of the knee actuator and a first port of the hip actuator in a first position; blocking fluid communication between the knee actuator and the fluid circuit and between the first and second ports of the knee actuator in a second position; enabling fluid communication between the first port of the knee actuator and the first port of the hip actuator and between the second port of the knee actuator and the second port of the hip actuator in a third position; and enabling fluid communication between the first and second ports of the knee actuator while blocking fluid communication between the knee actuator and the hip actuator in a fourth position.

15. The orthotic device of claim 1, wherein the pump and hip actuator are located on the hip link.

16. The orthotic device of claim 15, wherein the pump and hip actuator are located, at least partially, within the hip link.

17. The orthotic device of claim 15, wherein both the pump and the motor are located on the hip link so as to be behind a user's body.

18. A lower limb orthotic device adapted to be worn by a user comprising:

a thigh link adapted to couple to a user's lower limb;

a hip link;

a hip joint rotatably coupling the thigh link and the hip link through a first range of motion;

a shank link adapted to be coupled to a user's lower limb;

a knee joint rotatably coupling the thigh link to the shank link through a second range of motion;

a hip torque generator including a hip actuator and a first mechanical transmission mechanism including a multi-bar linkage having at least first, second and third pivoting links, connected to the hip actuator, with the hip actuator and the first mechanical transmission mechanism being interposed between the thigh link and the hip link; and an electric motor for providing mechanical energy to the hip torque generator, said electric motor being adapted to be positioned behind the user's body so as to minimize space taken by the orthotic device on a side of the user.

19. The orthotic device of claim 18, wherein the first mechanical transmission mechanism further includes a fourth link.

20. The orthotic device of claim 19, wherein the fourth link of the first mechanical transmission mechanism establishes a fixed pivot axis for the hip joint.

21. The orthotic device of claim 18, wherein the orthotic device establishes multiple effective gear ratios in order to provide for a first motion through the first range of motion at a first torque during a swing phase of the orthotic device and a second motion through the first range of motion at a second torque during a stance phase of the orthotic device, wherein the second motion is slower than the first motion and the second torque is higher than the first torque.

22. A lower limb orthotic device adapted to be worn by a user comprising:

a thigh link adapted to couple to a user's lower limb;

a hip link;

a hip joint rotatably coupling the thigh link and the hip link to allow flexion and extension between the thigh link and the hip link through a first range of motion;

a power source;

a hip torque generator interconnected between the thigh link and the hip link, the hip torque generator including:

a hip actuator; and a first mechanical transmission mechanism connected to the hip actuator, wherein the first mechanical transmission mechanism includes a multi-bar linkage having at least first, second and third pivoting links, with the hip actuator and the first mechanical transmission mechanism being interposed between the thigh link and the hip link;

a shank link adapted to be coupled to a user's lower limb, said shank link being rotatably coupled to the thigh link via a knee joint;

a knee torque generator coupled to the thigh link and the shank link, the knee torque generator including:

a knee actuator; and a second mechanical transmission mechanism connecting the knee actuator to the shank link; and an electric motor configured to be drivingly connected to each of the hip actuator and the knee actuator so as to provide torque to both the hip and knee actuators without an energy dissipating device between the electric motor and the hip and knee actuators.

23. A lower limb orthotic device adapted to be worn by a user comprising:

a thigh link adapted to couple to a user's lower limb;

a hip link;

a hip joint rotatably coupling the thigh link and the hip link to allow flexion and extension between the thigh link and the hip link through a first range of motion;

a power source;

a hip torque generator interconnected between the thigh link and the hip link, the hip torque generator including:

a hip actuator; and a first mechanical transmission mechanism connected to the hip actuator, wherein the first mechanical transmission mechanism includes a multi-bar linkage having at least first, second and third pivoting links, with the hip actuator and the first mechanical transmission mechanism being interposed between the thigh link and the hip link;

a shank link adapted to be coupled to a user's lower limb, said shank link being rotatably coupled to the thigh link via a knee joint;

a knee torque generator coupled to the thigh link and the shank link, the knee torque generator including:

a knee actuator; and a second mechanical transmission mechanism connecting the knee actuator to the shank link; and an electric motor drivingly connected to the hip actuator wherein, during normal use, the electric motor provides energy for the orthotic device and the knee actuator acts as an energy dissipating device.

24. The orthotic device of claim 23 wherein said hip joint generator and said knee torque generator are configured such that, when a user of the orthotic device ascends stairs or a steep slope, said electric motor provides energy to both the hip actuator and the knee actuator.

25. A method of operating a lower limb orthotic device including a thigh link coupled to a user's lower limb, a hip link supported by the user, a hip joint rotatably coupling the thigh link and the hip link to allow flexion and extension between the thigh link and the hip link through a first range of motion, a shank link coupled to a user's lower limb and a knee joint rotatably coupling the thigh link to the shank link through a second range of motion, said method comprising:

activating a hip torque generator, including a hip actuator and a first mechanical transmission mechanism connected to the hip actuator, to cause relative motion between the thigh link and the hip link, wherein the first mechanical transmission mechanism includes a multi-bar linkage having at least first, second and third pivoting links;

activating a knee torque generator, including a knee actuator and a second mechanical transmission mechanism connected to the knee actuator, to cause relative motion between the thigh link and the shank link; and controlling, through a common electric motor and pump linked to each of the hip and knee torque generators, both the hip torque generator and the knee torque generator for regulating relative positions both between the thigh link and hip link within the first range of motion through the hip actuator and the first mechanical transmission mechanism, and between the thigh link and the shank link within the second range of motion through the knee actuator and the second mechanical transmission mechanism, in order to cause the lower limb orthotic device to power a user through a natural walking motion.

26. The method of claim 25, further comprising: controlling the hip torque generator to provides for a first motion through the first range of motion at a first torque during a swing phase of the orthotic device and a second motion through the first range of motion at a second torque during a stance phase of the orthotic device, wherein the second motion is slower than the first motion and the second torque is higher than the first torque.

27. The method of claim 25, wherein moving the orthotic device through the first and second ranges of motion includes shifting a multi-bar linkage established by at least first, second and third pivoting links for each of the first and second mechanical transmission mechanisms.

28. A lower limb orthotic device adapted to be worn by a user comprising:

a thigh link adapted to couple to a user's lower limb;

a hip link;

a hip joint rotatably coupling the thigh link and the hip link to allow flexion and extension between the thigh link and the hip link through a range of motion;

a power source; and a hip torque generator interconnected between the thigh link and the hip link, the hip torque generator including:

a hip actuator; and a mechanical transmission mechanism, including a multi-bar linkage having at least first, second and third pivoting links, connected to the hip actuator, with the hip actuator and the mechanical transmission mechanism being interposed between the thigh link and the hip link;

a fluid circuit fluidly connected to the hip actuator;

a pump adapted to develop a flow of fluid in the fluid circuit; and an electric motor drivingly connected to the pump to cause pressurized fluid within the fluid circuit to alter relative positions of the thigh link and hip link within the range of motion through both the hip actuator and the mechanical transmission mechanism, with the mechanical transmission mechanism aiding in evening out torque over the range of motion.

29. The orthotic device of claim 28, wherein the mechanical transmission mechanism further includes a fourth link, said fourth link establishing a fixed pivot axis for the hip joint.

* * * * *